(12) United States Patent
Nicolaides et al.

(10) Patent No.: US 7,319,036 B2
(45) Date of Patent: Jan. 15, 2008

(54) METHOD FOR GENERATING HYPERMUTABLE ORGANISMS

(75) Inventors: Nicholas C. Nicolaides, Boothwyn, PA (US); Philip M. Sass, Audubon, PA (US); Luigi Grasso, Philadelphia, PA (US); Bert Vogelstein, Baltimore, MD (US); Kenneth W. Kinzler, Bel Air, MD (US)

(73) Assignees: The Johns Hopkins University School of Medicine, Baltimore, MD (US); Morphotek, Inc., Philadelphia, PA (US)

( * ) Notice: Subject to any disclaimer, the term of this patent is extended or adjusted under 35 U.S.C. 154(b) by 198 days.

(21) Appl. No.: 10/873,114

(22) Filed: Jun. 23, 2004

(65) Prior Publication Data

US 2005/0188428 A1 Aug. 25, 2005

Related U.S. Application Data

(62) Division of application No. 09/853,646, filed on May 14, 2001, now Pat. No. 6,825,038.

(60) Provisional application No. 60/204,769, filed on May 17, 2000, provisional application No. 60/203,905, filed on May 12, 2000.

(51) Int. Cl.
C12N 15/00 (2006.01)
C12N 5/00 (2006.01)
C12N 15/63 (2006.01)

(52) U.S. Cl. ............... 435/440; 435/455; 435/456; 435/320.1; 435/325

(58) Field of Classification Search ............... 435/440, 435/455, 456, 320.1, 325
See application file for complete search history.

(56) References Cited

U.S. PATENT DOCUMENTS

| | | | |
|---|---|---|---|
| 5,907,079 A | 5/1999 | Mak et al. | |
| 6,146,894 A | 11/2000 | Nicolaides et al. | |
| 6,191,268 B1 | 2/2001 | Liskay et al. | |
| 6,287,862 B1 | 9/2001 | delCardayre et al. | |
| 6,825,038 B2 * | 11/2004 | Nicolaides et al. | 435/440 |

FOREIGN PATENT DOCUMENTS

| | | |
|---|---|---|
| CA | 2240609 | 10/1999 |
| WO | WO 94/29442 | 12/1994 |
| WO | WO 95/15381 | 6/1995 |
| WO | WO 96/01313 | 1/1996 |
| WO | WO 97/08312 | 3/1997 |
| WO | WO 99/19492 | 4/1999 |
| WO | WO 01/59092 | 8/2001 |
| WO | WO 01/62945 | 8/2001 |

OTHER PUBLICATIONS

Kappel et al. Current Biology, 1992, 3: 548-553.*
Mullins et al. Hypertension, 1993, 22: 630-633.*
Houdebine et al. Journal of Biotechnology, 1994, 34: 269-287.*
Wall R.J. Theriogenology, 1996, 45: 57-68.*
Mullins et al. Journal of Clinical Investigation, 1996, 98(11): S37-S40.*
Cameron E. Molecular Biology, 1997, 7: 253-265.*
Sigmund C. Arterioscler. Thromb. Vasc. Biol., 2000, 20: 1425-1429.*
Niemann H. Transgenic Research, 1998, 7: 73-75.*
Buermeyer, Andrew B., et al., "The Human *HLH1* cDNA Complements DNA Mismatch Repair Defects in M1H1-deficient Mouse Embryonic Fibroblasts," Cancer Research, Feb. 1, 1999, pp. 538-541, vol. 59., No. 3.
Cascalho, Marilia, et al., "Mismatch Repair Co-oped by Hypermutation," Science, pp. 1207-1210, Feb. 20, 1998, vol. 279, Lancaster, PA.
Iaccarino, Ingram, et al., hMSH2 and hMSH6 play distinct roles in mismatch binding and contribute differently to the ATPase activity of hMutSα, The EMBO Journal, pp. 2677-2686, May 1, 1998, vol. 17, No. 9, Oxford University Press.
Lipkin, Steven M.., et al., "*MLH3*: a DNA mismatch repair gene associated with mammalian microsatellite instability," Nature Genetics, pp. 27-35, Jan. 2000, vol. 24, No. 1, Nature America, New York, NY.
Nicolaides, Nicolas C., et al., "A Naturally Occurring *hPMS2* Mutation Can Confer a Dominant Negative Mutator Phenotype," Molecular and Cellular Biology, pp. 1635-1641, Mar. 1998, Vo. 18, No. 3, American Society for Microbiology, Washington, D.C.
Risinger, John I., et al., Single Gene Complementation of the *hPMS2* Defect in HEC-1-A Endometrial Carcinoma Cells, Cancer Research, pp. 2978-2981, Jul. 15, 1998, vol. 58, No. 14.
Allen, D., et al., "MutS mediates heteroduplex loop formation by a translocation mechanism" *EMBO J.*, 1997, 16(14), 4467-4476.
Baker, S.M., et al., "Male mice defective in the DNA mismatch repair gene PMS2 exhibit abnormal chromosome synapsis in meiosis" *Cell*, 1995, 82, 309-319.
Bronner C.E., et al., "Mutation in the DNA mismatch repair gene homologue hMLH1 is associated with hereditary non-polyposis colon cancer" *Nature*, 1994, 368, 258-261.
de Wind, N., et al., "Inactivation of the mouse Msh2 gene results in mismatch repair deficiency, methylation tolerance, hyper-recombination, and predisposition to cancer" *Cell*, 1995, 82, 321-330.
Drummond, J.T., et al., "Isolation of an hMSH2-p160 heterodimer that restores DNA mismatch repair to tumor cells" *Science*, 1995, 268, 1909-1912.

(Continued)

*Primary Examiner*—Valarie Bertoglio
*Assistant Examiner*—Wu-Cheng Winston Shen
(74) *Attorney, Agent, or Firm*—Banner & Witcoff, Ltd.

(57) ABSTRACT

Dominant negative alleles of human mismatch repair genes can be used to generate hypermutable cells and organisms. By introducing these genes into cells and transgenic animals, new cell lines and animal varieties with novel and useful properties can be prepared more efficiently than by relying on the natural rate of mutation. The enhanced rate of mutation can be further augmented using mutagens. Moreover, the hypermutability of mismatch repair deficient cells can be remedied to stabilize cells or mammals with useful mutations.

17 Claims, 12 Drawing Sheets

OTHER PUBLICATIONS

Drummond, J.T., et al., "Cisplatin and adriamycin resistance are associated with mutlα and mismatch repair deficiency in an ovarian tumor cell line" *J. Biological Chemistry*, 1996, 271(33), 19645-19648.

Edelmann, W., et al., "Meiotic pachytene arrest in MLH1-deficient mice" *Cell*, 1996, 85, 1125-1134.

Eshleman, J.R., et al., "Mismatch repair defects in human carcinogenesis" *Human Molecular Genetics*, 1996, 5, 1489-1494.

Fishel, R. et al. "The human mutator gene homolog MSH2 and its association with hereditary nonpolyposis colon cancer." *Cell* 1993, 7:1027-1038.

Galio, L., et al., "ATP hydrolysis-dependent formation of a dynamic ternary nucleoprotein complex with MutS and MutL" *Nucleic Acids Research*, 1999, 27(11), 2325-2331.

Hamilton, S.R. et al. "The molecular basis of Turcot's syndrome." *N. Eng. J. Med*. 1995, 332:839-847.

Harfe, B.D., "DNA mismatch repair and genetic instability" *Annu. Rev. Genet.*, 2000, 34, 359-399.

Hoang J., et al., "BAT-26, an Indicator of the Replication Error Phenotype in Colorectal Cancers and Cell Lines" *Cancer Res.*, 1997, 57, 300-303.

Holmes, J., S. Clark, and P. Modrich. "Strand-specific mismatch correction in nuclear extracts of human and *Drosophila melanogaster* cell lines" *Proc. Natl. Acad. Sci. USA* 1990 87:5837-5841.

Honma, M. et al., "Cytotoxic and Mutagenic Responses to X-rays and Chemical Mutagens in Normal and p53-mutated Human Lymphoblastoid Cells" *Mut. Res.*, 1997, 374, 89-98.

Jiricny, J., et al., "Mismatch repair defects in cancer" *Curr. Opin. Genet. Dev.*, 2000, 10, 157-161.

Karran, P., et al., "Genomic instability and tolerance to alkylating agents" *Cancer Surveys*, 1996, 28, 69-71.

Leach, F.S., et al., "Mutations of a mutS homolog in hereditary nonpolyposis colorectal cancer" *Cell*, 1993, 75, 1215-1225.

Li, G.-M. and P. Modrich. "Restoration of mismatch repair to nuclear extracts of H6 colorectal tumor cells by a heterodimer of human MutL homologs" *Proc. Natl. Acad. Sci. USA* 1995 92:1950-1954.

Liu, T., et al., "Microsatellite instability as a predictor of a mutation in a DNA mismatch repair gene in familial colorectal cancer" *Genes, Chromosomes & Cancer*, 2000, 27, 17-25.

Liu et al., "Analysis of Mismatch Repair Genes in Hereditary Non-polyposis Colorectal Cancer Patients" *Nature Medicine*, Feb. 1996, 2(2), 169-174.

Ma et al., "Dominant Negative Expression of hPMS2 Creates Isogenic Mismatch Repair Deficient Human Colon Cancer Cell Lines" *Proc. Am. Assoc. Cancer Res.*, Mar. 1998, 39, p. 460 (Abstract #3130).

McCallum, C.M., "Targeted screening for induced mutations" *Nature Biotechnology*, 2000, 18, 455-457.

Modrich, P., "Mismatch repair, genetic stability, and cancer" *Science*, 1994, 266, 1959-1960.

Nicolaides, N.C., et al., "The jun family members, c-jun and junD, transactivate the human c-*myb*, promotor via an Ap1-like element" *J. Biological Chemistry*, 1992, 267(27), 19655-19672.

Nicolaides, N.C., et al., "Genomic organization of the human *PMS2* gene family" *Genomics*, 1995, 30, 195-206.

Nicolaides, N.C. et al. "Molecular cloning of the N- terminus of GTBP." *Genomics* 1996, 31:395-397.

Nicolaides, N.C., et al., "Positive autoregulation of c-*myb*, expression via Myb binding sites in the 5' flanking region of the human c-*myb* gene" *Molecular and Cellular Biology*, 1991, 11(12), 6166-6176.

Nicolaides, N.C., et al., "Analysis of the 5' region of *PMS2* reveals heterogeneous transcripts and a novel overlapping gene" *Genomics*, 1995, 29, 329-334.

Nicolaides, N.C., et al., "Mutations of two PMS homologues in hereditary nonpolyposis colon cancer" *Nature*, 1994, 371, 75-80.

Palombo, F., et al., "Mismatch repair and cancer" *Nature*, 1994, 367, 417.

Pang, Q., T.A. Prolla and R.M. Liskay, "Functional domains of the *Saccharomyces cerevisiae* Mlh1p and Pms1p DNA mismatch repair proteins and their relevance to human hereditary nonpolyposis colorectal cancer-associated mutations" *Mol. Cell. Biol.* 1997 17(8):4465-4473.

Papadopoulos, N., et al., "Mutation of a *mutL* homolog in hereditary colon cancer" *Science*, 1994, 263, 1625-1629.

Papadopoulos, N., et al., "Mutations of *GTBP* in genetically unstable cells" *Science*, 1995, 268, 1915-1917.

Parsons, R. et al. "Mismatch repair deficiency in phenotypically normal human cells." *Science* 1995 268:738-740.

Parsons, R., et al., "Hypermutability and mismatch repair deficiency in RER+ tumor cells" *Cell*, 1993, 75, 1227-1236.

Peinado, M.A., et al., "Isolation and characterization of allelic losses and gains in colorectal tumors by arbitrarily primed polymerase chain reaction" *Proc. Natl. Acad. Sci. USA*, 1992, 89, 10065-10069.

Perucho, M., et al., "Cancer of the microsatellite mutator phenotype" *Biol. Chem.*, 1996, 377, 675-684.

Prolla, T.A., et al., "MLH1, PMS1, and MSH2 interactions during the initiation of DNA mismatch repair in yeast" *Science*, 1994, 265, 1091-1093.

Quian, Y. et al., "Molecular events after antisense inhibition of hMSH2 in a HeLa cell line" *Mutation Research*, Oct. 12, 1998, vol. 418, pp. 61-71.

Spampinato, C., et al., "The MutL ATPase is required for mismatch repair" *J. Biological Chemistry*, 2000, 275(13), 9863-9869.

Strand, M., et al., "Destabilization of tracts of simple repetitive DNA in yeast by mutations affecting DNA mismatch repair" *Nature*, 1993, 365, 274-276.

Su, S., et al., "Mispair specificity of methyl-directed DNA mismatch correction in vitro" *J. Biological Chemistry*, 1988, 263(14), 6829-6835.

Vora, K.A. et al., "Severe Attenuation of the B Cell Immune Response in Msh2-deficient Mice" *Journal of Experimental Medicine*, Feb. 1999, 189(3), 471-481.

Wheeler, J.M.D., et al., "The role of hypermethylation of the *hMLH1* promoter region in HNPCC versus MSI+sporadic colorectal cancers" *J. Med. Genet.*, 2000, 588-592.

Winter, D.B. et al., "Altered spectra of hypermutation in antibodies from mice deficient for the DNA mismatch repair protein PMS2" *Proc. Natl. Acad. Sci., USA*, Jun. 1998, 95, 6953-6958.

Nicolaides, N.C., "A naturally occurring *hPMS2* mutation can confer a dominant negative nutator phenotype" *Mol. Cell. Biol.*, 1998, 18(3), 1635-1641.

* cited by examiner

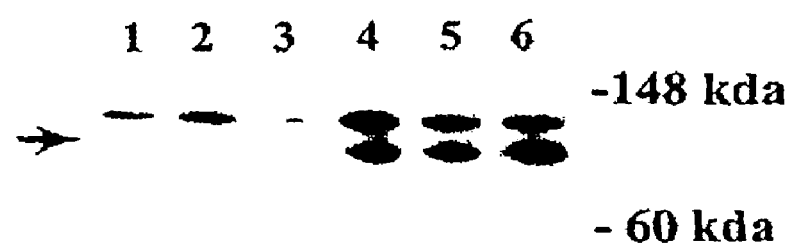
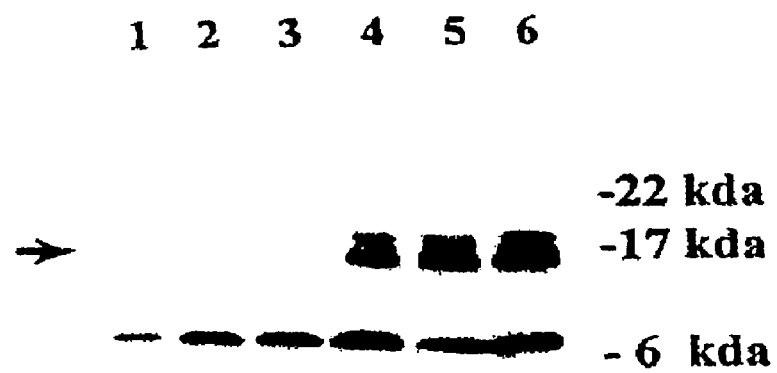

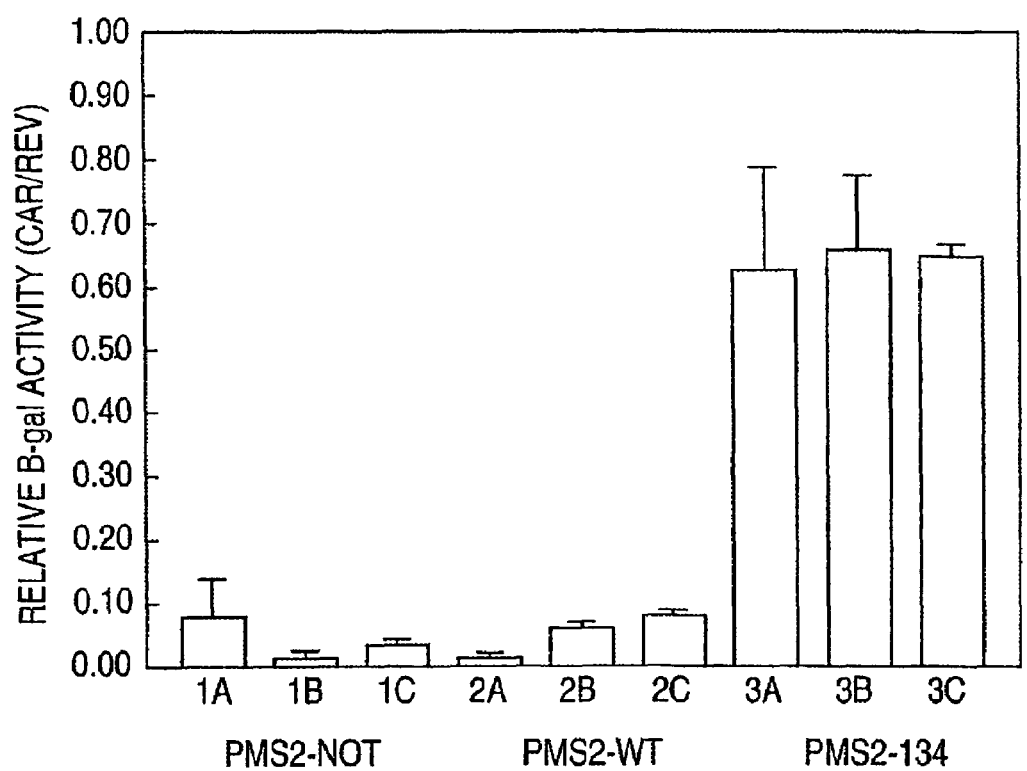

PMS2-134

PMS2-WT

AMP= ampicillin resistance gene
ERE= ecdysone response elements
MIN HSP PRO= minimal heat shock promoter
hPMS134= dominant negative MMR allele
polyA= BGH polyadenylation signal
NEO= neomycin phosphotrasferase gene

FIG. 7
polyPNP: out-of-frame polyA tract encodes for a truncated polypeptide
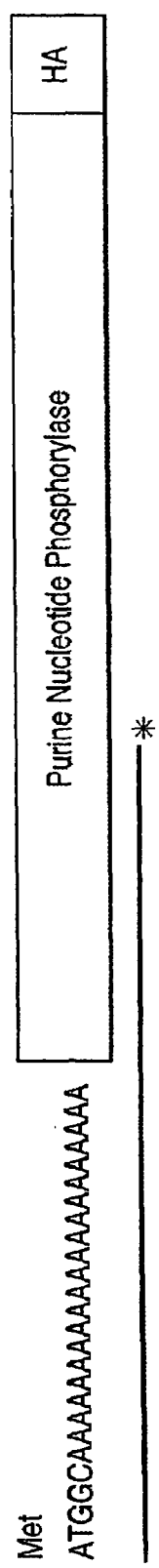
Met
ATGGCAAAAAAAAAAAAAAAAAAAAA
PNP: in-frame polyA tract encodes for a full-length polypeptide
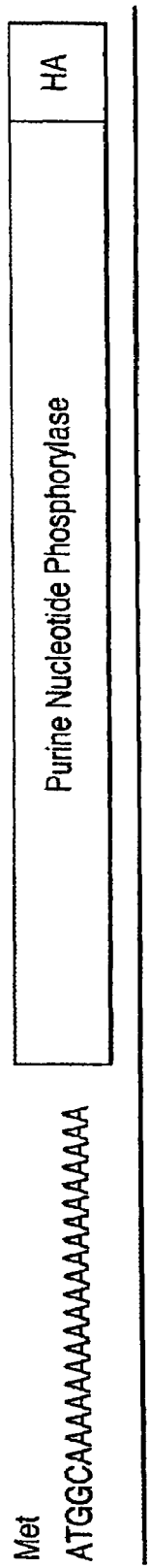
Met
ATGGCAAAAAAAAAAAAAAAAAAAAA

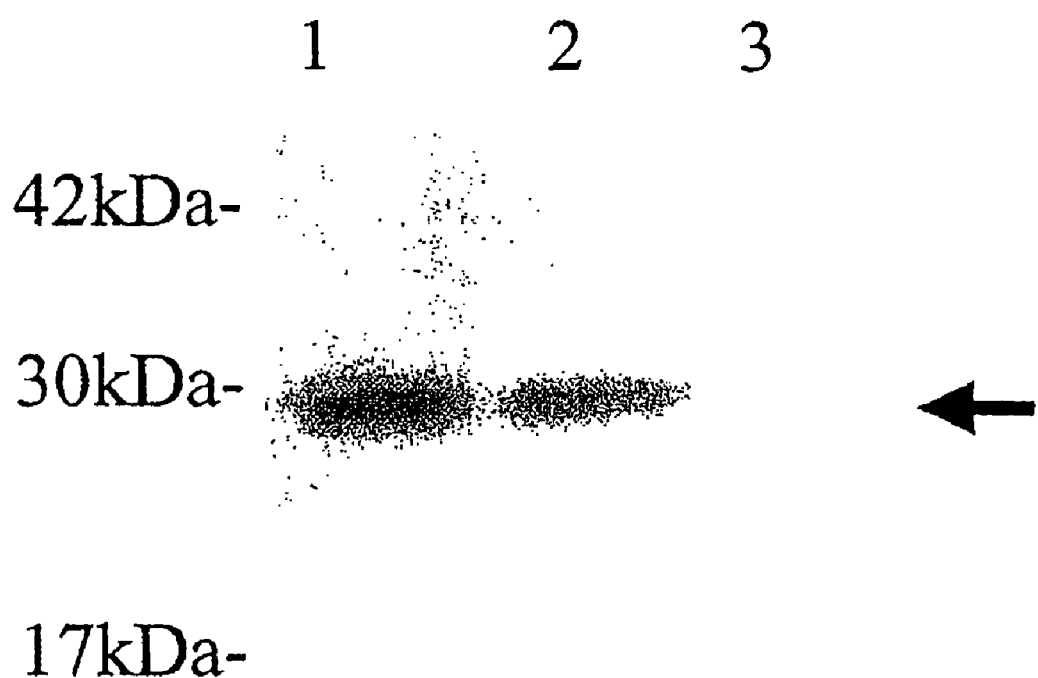

SEQUENCE LISTING

```
<160> NUMBER OF SEQ ID NOS: 4

<210> SEQ ID NO 1
<211> LENGTH: 64
<212> TYPE: DNA
<213> ORGANISM: Artificial Sequence
<220> FEATURE:
<223> OTHER INFORMATION: PCR primer

<400> SEQUENCE: 1
ccaagcttag accaccatgg caaaaaaaaa aaaaaaaaaa aatcgctacc ccacacatta      60
atgc                                                                  64

<210> SEQ ID NO 2
<211> LENGTH: 87
<212> TYPE: DNA
<213> ORGANISM: Artificial Sequence
<220> FEATURE:
<223> OTHER INFORMATION: PCR primer
```

```
<400> SEQUENCE: 2
ataagaatgc ggccgctatc cttagctagc gtaatctgga acatcgtaag cgtaatctgg    60
aacatcgtac tctttatcgc ccagcag                                        87

<210> SEQ ID NO 3
<211> LENGTH: 26
<212> TYPE: DNA
<213> ORGANISM: Artificial Sequence
<220> FEATURE:
<223> OTHER INFORMATION: Recombinant DNA

<400> SEQUENCE: 3
atggcaaaaa aaaaaaaaaa aaaaaa                                         26

<210> SEQ ID NO 4
<211> LENGTH: 25
<212> TYPE: DNA
<213> ORGANISM: Artificial Sequence
<220> FEATURE:
<223> OTHER INFORMATION: Recombinant DNA

<400> SEQUENCE: 4
atggcaaaaa aaaaaaaaaa aaaaa                                          25
```

METHOD FOR GENERATING HYPERMUTABLE ORGANISMS

This application is a divisional application of U.S. Ser. No. 09/853,646, filed May 14, 2001, now U.S. Pat. No. 6,825,038, which claims the benefit of 60/203,905 filed May 12, 2000 and 60/204,769 filed May 17, 2000, the disclosures of which are explicitly incorporated herein.

TECHNICAL FIELD OF THE INVENTION

The invention is related to the area of mismatch repair genes. In particular it is related to the field of mutagenesis.

BACKGROUND OF THE INVENTION

Within the past four years, the genetic cause of the Hereditary Nonpolyposis Colorectal Cancer Syndrome (HNPCC), also known as Lynch syndrome II, has been ascertained for the majority of kindreds affected with the disease (13). The molecular basis of HNPCC involves genetic instability resulting from defective mismatch repair (MMR). Many genes have been identified in rodents and humans that encode for proteins that appear to participate in the MMR process, including the mutS homologs GTBP, hMSH2, and hMSH3 and the mutL homologs hMLH1, hPMS1, and hPMS2 (2, 7, 11, 17, 20, 21, 22, 24). Germ line mutations in four of these genes (hMSH2, hMLH1, hPMS1, and hPMS2) have been identified in HNPCC kindreds (2, 11, 13, 17, 24). Though the mutator defect that arises from the MMR deficiency can affect any DNA sequence, microsatelite sequences are particularly sensitive to MMR abnormalities (14). Microsattelite instability is therefore a useful indicator of defective MMR. In addition to its occurrence in virtually all tumors arising in HNPCC patients, Microsattelite instability is found in a small fraction of sporadic tumors with distinctive molecular and phenotypic properties (27).

HNPCC is inherited in an autosomal dominant fashion, so that the normal cells of affected family members contain one mutant allele of the relevant MMR gene (inherited from an affected parent) and one wildtype allele (inherited from the unaffected parent). During the early stages of tumor development, however, the wildtype allele is inactivated through a somatic mutation, leaving the cell with no functional MMR gene and resulting in a profound defect in MMR activity. Because a somatic mutation in addition to a germ-line mutation is required to generate defective MMR in the tumor cells, this mechanism is generally referred to as one involving two hits, analogous to the biallelic inactivation of tumor suppressor genes that initiate other hereditary cancers (11, 13, 25). In line with this two hit mechanism, the non-neoplastic cells of HNPCC patients generally retain near normal levels of MMR activity due to the presence of the wildtype allele.

A wide range of organisms with defective MMR have been found to have widespread genetic mutations throughout their genome. In all cases, these organisms have germ-line mutations within both copies of a particular MMR gene. Recently, work done by Nicolaides et al have shown that a decrease in MMR can be achieved within cells from higher order organisms by introducing a dominant negative allele of a MMR gene. These data suggest that the use of such an approach can generate genetically altered organisms to produce new output traits. There is a need in the art for additional methods with which to generate genetic diversity.

SUMMARY OF THE INVENTION

It is an object of the present invention to provide a method for rendering cells hypermutable.

It is another object of the present invention to provide genetically altered cell lines.

It is another object of the present invention to provide phenotypically altered cell lines.

It is yet another object of the present invention to provide a method to produce an enhanced rate of genetic hypermutation in a cell.

It is a further object of the invention to provide a method of mutating a gene(s) of interest in a cell.

It is a further object of the invention to claim composition of matter for a genetically altered bacterial purine phosphorlyase.

It is a further object of the invention to claim composition of matter for a genetically altered bacterial purine phosphorlyase as a diagnostic tool for monitoring mismatch repair deficiency of a eucaryotic cell.

It is a further object of the invention to claim composition of matter for a generating genetically altered genes by incorporating a polymononucleotide tract to measure for altered mismatch repair in eucaryotic cells.

Yet another object of the invention is to provide a method of creating cells with new phenotypes.

Yet another object of the invention is to provide a method of creating cells with new phenotypes and a stable genome.

Yet another object of the invention is to provide a method of regulating the genetic stability of a cell or organism's genome.

It is a further object of the invention to generate hypermutable cell lines using inducible vectors containing dominant negative mismatch repair gene mutants.

It is a further object of the invention to screen for hypermutable cell lines containing inducible vectors with dominant negative mismatch repair gene mutants under induced gene expression conditions.

It is a further object of the invention to screen for hypermutable cell lines containing inducible vectors with dominant negative mismatch repair gene mutants under induced gene expression conditions for altered gene structure and/or new phenotypes.

It is a further object of the invention to turn off expression of a dominant negative MMR gene in cells containing structurally altered target genes and/or new phenotypes to restore genomic stability.

It is a further object of the invention to screen hypermutable cell lines containing an inducible vector comprising a dominant negative mismatch repair gene mutant under inducing conditions in the presence of chemical mutagens or ionizing radiation for structurally altered target genes and/or new phenotypes. Cells containing altered gene structure and/or new phenotype are then removed from inducer molecule and genetic stability is restored.

These and other objects of the invention are provided by one or more of the embodiments described below. In one embodiment of the invention, a method for making a hypermutable cell is provided. A polynucleotide encoding a dominant negative allele of a mismatch repair gene is introduced into a cell. The cell becomes hypermutable as a result of the introduction of the gene.

In another embodiment of the invention, an isolated hypermutable cell will be provided. The cell comprises a dominant negative allele of a mismatch repair gene. The cell is exposed to DNA akylating agents. The cell exhibits an enhanced rate of hypermutation.

In another embodiment of the invention, a method is provided for introducing a mutation into a gene of interest. A polynucleotide encoding a dominant negative allele of a mismatch repair gene is introduced into a cell. The cell becomes hypermutable as a result of the introduction of the gene. The cell further comprises a gene of interest. The cell is grown. The cell is tested to determine whether the gene of interest harbors a mutation.

In another embodiment of the invention, a method is provided for inserting a polymononucleotide tract in a gene to measure for mismatch repair activity of a eucaryotic cell. A polynucleotide tract is inserted out-of-frame into the coding region of a gene or a cDNA. The gene is introduced into a cell. The polymononucleotide tract is altered by mismatch repair deficiency. An in-frame altered gene is produced.

In another embodiment of the invention, a method is provided for producing new phenotypes of a cell. A polynucleotide encoding a dominant negative allele of a mismatch repair gene is introduced into a cell. The cell becomes hypermutable as a result of the introduction of the gene. The cell is grown. The cell is tested for the expression of new phenotypes. Another embodiment of the invention is the use of cells containing an inducible vector consisting of a dominant negative mismatch repair gene mutants under inducing conditions in the presence of chemical mutagens or ionizing radiation for altered target genes and/or new phenotypes. Cells containing altered gene structure and/or new phenotype are then removed from inducer molecule and genetic stability is restored. The cells are now used for commercial properties such as but not limited to recombinant manufacturing and/or gene discovery.

Another embodiment of the invention is the use of MMR defective cells containing a gene of interest in the presence of chemical mutagens or ionizing radiation for altered target genes and/or new phenotypes. Cells containing altered gene structure and/or new phenotype are then stably transduced with a wildtype MMR complementing gene and genetic stability is restored. The cells are now used for recombinant manufacturing or gene discovery.

In another embodiment of the invention, a method is provided for restoring genetic stability in a cell with defective mismatch repair gene. The activity of the mismatch repair process is restored and its genome is stable.

In another embodiment of the invention, a method is provided for restoring genetic stability in a cell with defective mismatch repair activity and a newly selected phenotype. The MMR deficiency can occur through the inactivation of endogenous MMR genes via genomic mutations or through the introduction of an eucaryotic expression vector producing a dominant negative MMR gene allele. In the case of cells lacking endogenous MMR due to a defect in an endogenous MMR gene, the cell is selected for a new phenotype or altered gene, RNA, or polypeptide. The cell becomes genetically stable through the introduction of a normal functioning MMR gene that complements the genomic defect of the host cell. This complementation group can include the use of any gene known to participate in mismatch repair deficiency. In the case were the expression of the dominant negative mismatch repair gene is used to induce DNA hypermutability, the dominant negative MMR gene expression will be suppressed by removal of the inducer molecule or by knocking out the expression of the dominant negative gene allele using standard gene knockout technology used by those skilled in the art (Waldman, T., et.al. *Cancer Res* 55:5187-5190, 1995). In any case, the cell restores its genetic stability and the new phenotype is stable.

These and other embodiments of the invention provide the art with methods that can generate enhanced mutability in organisms, cells and animals as well as providing genetically altered stable organisms cells and animals harboring potentially useful genome alterations.

The use of a dominant negative MMR gene allele is important in generating global mutations throughout the genome of a host organism in a regulated fashion. While the use of dominant negative alleles have been previously demonstrated to be capable of inducing global mutagenesis in a wide range of hosts (bacteria, yeast, mammals, plants) the use of inducible vectors to turn the dominant negative MMR gene mutant on to generate genome-wide mutation followed by selection for new biochemical output traits (e.g., resistance to chemical mutagens) and turning off of the dominant negative MMR gene allele to restore genetic stability is a new aspect of the invention. This method is now suitable for generating genetically diverse prokaryotic, eucaryotic and mammalian cells that can be screened for genetic mutations in genes involved in new phenotypes. In addition, this application teaches of the use of introducing dominant negative MMR alleles under control of inducible expression elements into MMR proficient cells. Stable or transiently transduced cells are then exposed to inducer molecule resulting in expression of the dominant negative MMR gene. Expression of the dominant negative product interferes with the endogenous MMR machinery, thereby causing genetic instability that leads to genetically diverse sublines. These cells are then put under specific selective assays and screened for new phenotypes and/or altered gene structures. After the establishment of sublines containing altered target genes and/or new phenotypes, cells are then rendered genetically stable by removal of the inducer molecule and a stable cell line is now produced that contains an altered gene and/or exhibits a new phenotype. This cell line can be used for gene discovery, drug target discovery, recombinant gene mutagenesis, and/or recombinant protein production.

It is well established that MMR deficient organisms are more tolerant to DNA damaging agents such as alkylating agents or ionizing radiation thereby leading to enhanced levels of genome-wide or locus-specific mutagenesis. Here we teach the use of exposing cell lines expressing dominant negative MMR under control of an inducible expression element to DNA damaging agents that can lead to enhanced genome wide mutagenesis. Cell lines are then screened for mutations in target genes or screened for novel phenotypes. Sublines with altered genes or phenotypes are then removed from inducer agent to "turn off" the dominant negative MMR gene allele to restore genetic stability. This cell line can be used for gene discovery, drug target discovery, recombinant gene mutagenesis, and/or recombinant protein production.

Finally, the use of mammalian cell lines that are naturally defective for MMR can be used to introduce a plasmid containing a gene of interest. The gene can be introduced and expressed transiently or stably. The cell now grows and the structure and/or function of the introduced gene is screened to identify those with structural and/or functional alterations. To enhance mutation rate, cells can be further exposed to DNA damaging agents such as but not limited to alkylating chemical mutagens or ionizing radiation to produce enhanced genome wide mutation rate in the host. Once a cell line(s) containing mutations within the gene of interest are generated, the cell is stably transduced with a gene that complements for the endogenous MMR defect. The cell line is now genetically stable and the cell line is suitable for producing altered gene products for gene discovery, recombinant gene mutagenesis, and/or recombinant protein production.

BRIEF DESCRIPTION OF THE DRAWINGS

FIG. 2A-2C. SH cells cotransfected with pCAR reporters and PMS2 expression vectors after 17 days of drug selection. (FIG. 2A) Western blots of lysates from untransfected SH cells (lane 1) or SH cells transfected with PMS2NOT (lane 2) or PMS2WT (lane 3). The arrow indicates the 110 kD protein expected for hPMS2. (FIG. 2B) Western blots of lysates from untransfected SH cells (lane 1) or SH cells transfected with PMS2NOT (lane 2) or PMS2134 (lane 3). The arrow indicates the 14 kD-protein expected for hPMS-134. Both A and B were probed with an antibody generated against the N terminus of hPMS2. The upper polypeptides in A and the lower polypeptides in B represent crossreactive hamster proteins. (FIG. 2C) β-galactosidase activity in lysates derived from SH cells cotransfected with PMS2NOT (lane 1), PMS2WT (lane 2), or PMS2134 (lane 3) plus reporter plasmid. Relative β-galactosidase activities are defined as the ratio of β-galactosidase activity in cells transfected with pCAROF compared to that in cells transfected with pCARIF; this normalization controlled for transfection efficiency and controlled for β-galactosidase activity in the cells expressing the various PMS2 effector genes.

FIG. 7. Diagram of the genetically altered purine phosphorlyase (PNP) gene with an out-of-frame poly A tract inserted in the N-terminus (referred to as polyPNP) (SEQ ID NO: 3). This gene encodes for a non-functional PNP gene. When the polyA tract is randomly altered by a defective MMR, the tract is shifted and allows for the production of a functional PNP gene. PNP can convert the non-toxic prodrug 9-(β-D-2-deoxyerythropentofuranosyl)—6-methylpurine (referred to as MPD) to the toxic 6-methyl purine analog (referred to as (MP). The construct has a hemaglutinin (HA) tag at the C-terminus for western blot analysis. A control construct with an in-frame polyA tract encoding a full-length polypeptide (SEQ ID NO: 4) is shown on the bottom.

FIGS. 8A and 8B. Toxicity assay of MMR defective or proficient cells expressing polyPNP with or without exposure to MPD. (FIG. 8A) Graph shows that in MMR-defective cells expressing the polyPNP gene, cells are killed in the presence of the MPD prodrug in contrast to MMR-proficient cells. (FIG. 8B) Western blot that shows production of a polyPNP-HA-tagged polypeptide in the MMR defective cells in contrast to MMR-proficient cells.

(FIG. 10A) Cell lysates from cells transfected with the MLHstop expression vector (lane 1) or the MLH1 vector (lane 2) were lysed and probed for MLH1 protein expression in HCT116 cells. As shown in FIG. 10A, the cells transfected with the MLH1 full-length expression construct produced a polypeptide of the expected molecular weight (arrow). (FIG. 10B) Cell lysates from HCT116 cells transfected with the MLHstop expression vector (lane 1) or the MLH1 vector (lane 2) plus the polyPNP gene were lysed and probed for polyPNP using an anti-HA monoclonal antibody that can detect the HA tag at the C-terminus of the PNP protein. As shown in FIG. 10B, the cells transfected with the MLHstop expression construct produced a polypeptide of the expected molecular weight (arrow) in contrast to cells transfected with the functional MLH1 cDNA, which restored genomic stability of the cell therefore maintaining the genomic structure of the polyPNP gene.

DETAILED DESCRIPTION OF THE INVENTION

Figure 1:
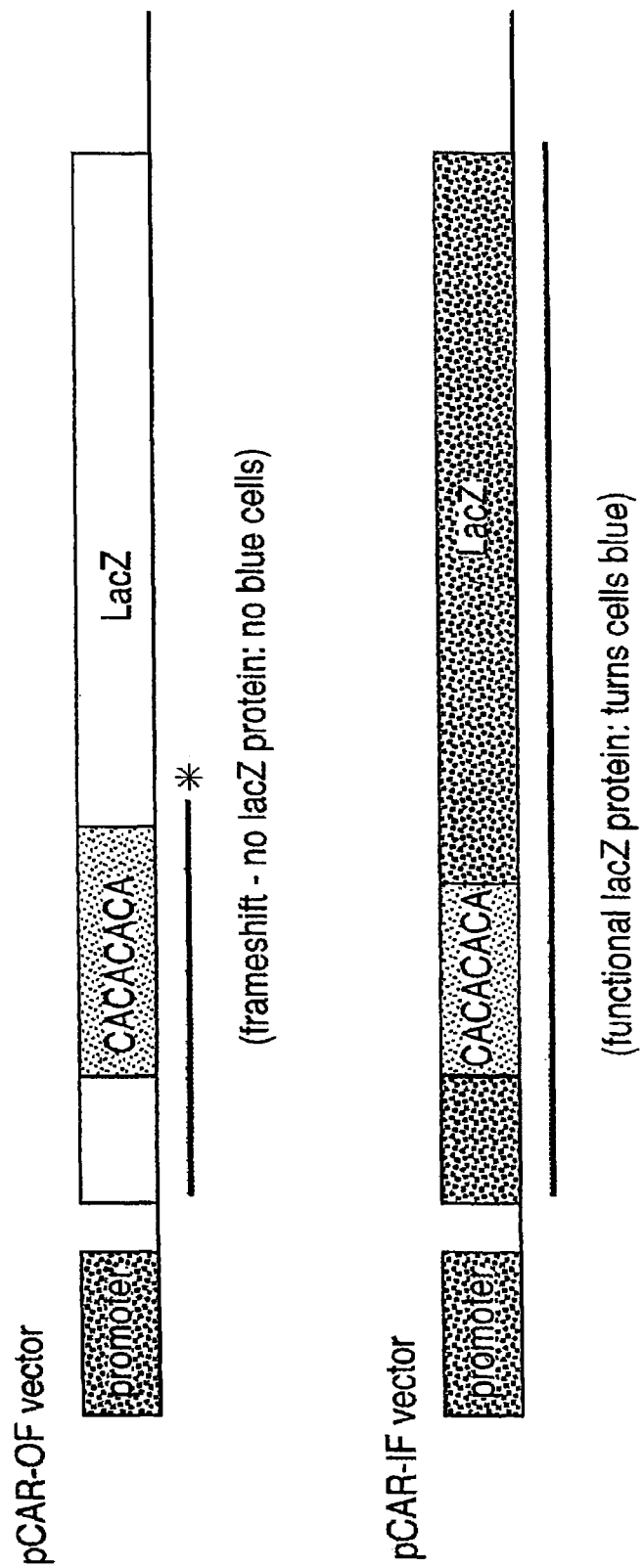
FIG. 1. Diagrams of pCAR reporters.

The inventors have discovered a method for developing hypermutable cells by taking advantage of cells with mismatch repair deficiency to create altered genes, RNAs, polypeptides and cells or whole organisms with new phenotypes. Dominant negative alleles of such genes, when introduced into cells or transgenic animals, increase the rate of spontaneous mutations by reducing the effectiveness of DNA repair and thereby render the cells or animals hypermutable. Hypermutable cells or animals can then be utilized to develop new mutations in a gene(s) to produce new output traits of a host cell or organism. The inventors will show that the use of chemical agents that cause damage to DNA can enhance the rate of hypermutability in cells expressing dominant negative mismatch repair gene alleles. The inventors also show that the selection of altered genes and restoration of genetic stability of a host cell or organism by restoring MMR can lead to stable biological products consisting of altered genes, RNAs, or polypeptides.

Protein complexes in cells ranging from bacteria to mammalian cells carry out the process of mismatch repair, also called mismatch proofreading. A mismatch repair gene is a gene that encodes one of the proteins of such a mismatch repair complex. Although not wanting to be bound by any particular theory of mechanism of action, a mismatch repair complex is believed to detect distortions of the DNA helix resulting from non-complementary pairing of nucleotide bases. The non-complementary base on the newer DNA strand is excised, and the excised base is replaced with the appropriate base which is complementary to the older DNA strand. In this way, cells eliminate many mutations that occur as a result of mistakes in DNA replication.

Dominant negative alleles cause a mismatch repair defective phenotype even in the presence of a wild-type allele in the same cell. An example of a dominant negative allele of a mismatch repair gene is the human gene hPMS2-134, which carries a truncation mutation at codon 134. The mutation causes the product of this gene to abnormally terminate at the position of the 134th amino acid, resulting in a shortened polypeptide containing the N-terminal 133 amino acids. Such a mutation causes an increase in the rate of mutations which accumulate in cells after DNA replication. Expression of a dominant negative allele of a mismatch repair gene results in impairment of mismatch repair activity, even in the presence of the wild-type allele. Any allele which produces such effect can be used in this invention.

Dominant negative alleles of a mismatch repair gene can be obtained from the cells of humans, animals, yeast, bacteria, or other organisms. Screening cells for defective mismatch repair activity can identify such alleles. Cells from animals or humans with cancer can be screened for defective mismatch repair. Cells from colon cancer patients may be particularly useful. Genomic DNA, cDNA, or mRNA from any cell encoding a mismatch repair protein can be analyzed for variations from the wild type sequence. Dominant negative alleles of a mismatch repair gene can also be created artificially, for example, by producing variants of the hPMS2-134 allele or other mismatch repair genes. Various techniques of site-directed mutagenesis can be used. The suitability of such alleles, whether natural or artificial, for use in generating hypermutable cells or animals can be evaluated by testing the mismatch repair activity caused by the allele in the presence of one or more wild-type alleles, to determine if it is a dominant negative allele.

A cell, an organism, or an animal into which a dominant negative allele of a mismatch repair gene has been introduced will become hypermutable. This means that the spontaneous mutation rate of such cells or animals is elevated compared to cells or animals without such alleles. The degree of elevation of the spontaneous mutation rate can be at least 2-fold, 5-fold, 10-fold, 20-fold, 50-fold, 100-fold, 200-fold, 500-fold, or 1000-fold that of the normal cell or animal.

According to one aspect of the invention, a polynucleotide encoding a dominant negative form of a mismatch repair protein is introduced into any eucaryotic cell or a transgenic animal. The gene can be any dominant negative allele encoding a protein, which is part of a mismatch repair complex, for example, PMS2, PMS1, MLH1, GTBP, MSH3 or MSH2. The dominant negative allele can be naturally occurring or made in the laboratory. The polynucleotide can be in the form of genomic DNA, cDNA, RNA, or a chemically synthesized polynucleotide. The polynucleotide can be cloned into an expression vector containing a constitutively active promoter segment (such as but not limited to CMV, SV40, EF-1α or LTR sequences) or to inducible promoter sequences such as the tetracycline, or ecdysone/glucocorticoid inducible vectors, where the expression of the dominant negative mismatch repair gene can be regulated. The polynucleotide can be introduced into the cell by transfection.

Transfection is any process whereby a polynucleotide is introduced into a cell. The process of transfection can be carried out in a living animal, e.g., using a vector for gene therapy, or it can be carried out in vitro, e.g., using a suspension of one or more isolated cells in culture. The cell can be any type of eucaryotic cell, including, for example, cells isolated from humans or other primates, mammals or other vertebrates, invertebrates, and single celled organisms such as protozoa or yeast.

In general, transfection will be carried out using a suspension of cells, or a single cell, but other methods can also be applied as long as a sufficient fraction of the treated cells or tissue incorporates the polynucleotide so as to allow transfected cells to be grown and utilized. The protein product of the polynucleotide may be transiently or stably expressed in the cell. Techniques for transfection are well known. Available techniques for introducing polynucleotides include but are not limited to electroporation, transduction, cell fusion, the use of calcium chloride, and packaging of the polynucleotide together with lipid for fusion with the cells of interest. Once a cell has been transfected with the mismatch repair gene, the cell can be grown and reproduced in culture. If the transfection is stable, such that the gene is expressed at a consistent level for many cell generations, then a cell line results.

An isolated cell is a cell obtained from a tissue of humans or animals by mechanically separating out individual cells and transferring them to a suitable cell culture medium, either with or without pretreatment of the tissue with enzymes, e.g., collagenase or trypsin. Such isolated cells are typically cultured in the absence of other types of cells. Cells selected for the introduction of a dominant negative allele of a mismatch repair gene may be derived from a eucaryotic organism in the form of a primary cell culture or an immortalized cell line, or may be derived from suspensions of single-celled organisms.

A polynucleotide encoding a dominant negative form of a mismatch repair protein can be introduced into the genome of an animal by producing a transgenic animal. The animal can be any species for which suitable techniques are available to produce transgenic animals. For example, transgenic animals can be prepared from domestic livestock, e.g., cows, pigs, sheep, goats, horses, etc.; from animals used for the production of recombinant proteins, e.g., cows, pigs, or goats that express a recombinant protein in their milk; or experimental animals for research or product testing, e.g., mice, rats, hamsters, guinea pigs, rabbits, etc.

Any method for making transgenic animals known in the art can be used. According to one process of producing a transgenic animal, the polynucleotide is injected into a fertilized egg of the animal and the injected egg is placed into a pseudo-pregnant female. The egg develops into a mature animal in which the polynucleotide is incorporated and expressed. The fertilized egg is produced in vitro from the egg and sperm of donor animals of the same species as the pseudo-pregnant female, who is prepared by hormone treatments to receive the fertilized egg and become pregnant. An alternative method for producing transgenic animals involves introducing the polynucleotide into embryonic cells by injection or transfection and reintroducing the embryonic cells into the developing embryo. With this method, however, if the polynucleotide is not incorporated into germ line cells, the gene will not be passed on to the progeny. Therefore, a transgenic animal produced by this method must be evaluated to determine whether the gene is incorporated into germ cells of the animal. Once transgenic animals are produced, they can be grown to reproductive age, when they can be mated to produce and maintain a colony of transgenic animals.

Once a transfected cell line or a colony of transgenic animals has been produced, it can be used to generate new mutations in one or more gene(s) of interest. A gene of interest can be any gene naturally possessed by the cell line or transgenic animal or introduced into the cell line or transgenic animal. An advantage of using such cells or animals to induce mutations is that the cell or animal may have a wide spectrum of genetic alterations that may produce commercially beneficial biological products. Hypermutable animals can then be bred and selected for new desired output traits (such as milk production, pest resistance, etc.). Once a new trait is identified, the dominant negative allele can be removed by directly knocking out the allele by technologies used by those skilled in the art or by breeding to mates lacking the dominant negative allele to select for offspring with a desired trait and a stable genome. Another alternative is to use a CRE-LOX expression system, whereby the dominant negative allele is spliced from the animal genome once a new output trait has been established.

Another aspect of the invention is the use of cells lacking MMR (due to mutated endogenous MMR gene or genes or through the introduction of a dominant negative MMR gene) and chemical mutagens to cause an enhanced rate of mutations in a host's genome. The lack of MMR activity has been known to make cells more resistant to the toxic effects of DNA damaging agents. This invention teaches of the use of making proficient MMR cells; mismatch repair defective via the expression of a dominant negative MMR gene allele and then enhancing the genomic hypermutability with the use of a DNA mutagen. This application also teaches us of the use of employing cells that are naturally deficient in MMR and exposure of chemical mutagens to increase the rate of genomic alterations to generate cells with new genetic structures and/or new phenotypes. Chemical mutagens are classifiable by chemical properties, e.g., alkylating agents, cross-linking agents, etc. The following chemical mutagens are useful, as are others not listed here, according to the invention. N-ethyl-N-nitrosourea (ENU), N-methyl-N-nitrosourea (MNU), procarbazine hydrochloride, chlorambucil, cyclophosphamide, methyl methanesulfonate (MMS), ethyl methanesulfonate (EMS), diethyl sulfate, acrylamide monomer, triethylene melamin (TEM), melphalan, nitrogen mustard, vincristine, dimethylnitrosamine, N-methyl-N'-nitro-Nitrosoguanidine (MNNG), 7,12 dimethylbenz (a) anthracene (DMBA), ethylene oxide, hexamethylphosphoramide, bisulfan. In a preferred aspect of the invention, a mutagenesis technique is employed that confers a mutation rate in the range of 1 mutation out of every 100 genes; 1 mutation per 1,000 genes. The use of such combination (MMR deficiency and chemical mutagens will allow for the generation of a wide array of genome alterations (such as but not limited to expansions or deletions of DNA segments within the context of a gene's coding region, a gene's intronic regions, or 5' or 3' proximal and/or distal regions, point mutations, altered repetitive sequences) that are preferentially induced by each particular agent.

Mutations can be detected by analyzing for alterations in the genotype of the cells or animals, for example by examining the sequence of genomic DNA, cDNA, messenger RNA, or amino acids associated with the gene of interest. Mutations can also be detected by screening the phenotype of the gene. An altered phenotype can be detected by identifying alterations in electrophoretic mobility, spectroscopic properties, or other physical or structural characteristics of a protein encoded by a mutant gene. One can also screen for altered function of the protein in situ, in isolated form, or in model systems. One can screen for alteration of any property of the cell or animal associated with the function of the gene of interest, such as but not limited to measuring protein secretion, chemical-resistance, pathogen resistance, etc.

Another invention of the application is the use of inducible vectors that control the expression of a dominant negative and normally functioning MMR gene. This application teaches of the utility of using such a strategy to restore DNA stability once a host cell or organism exhibiting a new output trait, altered gene, RNA or polypeptide has been generated via trait selection with or without the combination of chemical mutagens to establish a genetically stable version of this cell or organism. In the case of MMR defective cells as a result of ectopically expressing a dominant negative MMR gene allele, the MMR activity is decreased or completely eliminated by removing the inducer molecule from the cell culture or organism's environment. In addition, the expression of a dominant negative MMR gene can be suppressed by knocking out the MMR gene allele using methods that are standard to those skilled in the art of DNA knockout technology in germ or somatic cells (Waldman, T., et.al. *Cancer Res* 55:5187-5190, 1995).

Yet another invention teaches us of the use of restoring MMR activity in a MMR defective cell line such as HCT116, DLD-1, etc., whereby the cell is treated with chemical mutagens, selected for a new output trait such as pathogen-resistance, chemical-resistance, etc. The cell is then transfected with a copy of a wild type MMR gene that complements the endogenous MMR defect and restores DNA stability of a cell or an organism exhibiting a new output trait, an altered gene sequence, an altered RNA expression and/or an altered protein expression.

The above disclosure generally describes the present invention. A more complete understanding can be obtained by reference to the following specific examples which are provided herein for purposes of illustration only, and are not intended to limit the scope of the invention.

EXAMPLE 1

Use of Dominant Negative Mismatch Repair Protein to Cause Hypermutability in Mismatch Repair Proficient Cells A profound defect in MMR was found in the normal cells of two HNPCC patients. That this defect was operative in vivo was demonstrated by the widespread presence of microsattelite instability in nonneoplastic cells of such patients. One of the two patients had a germline truncating mutation of the hPMS2 gene at codon 134 (the hPMS2134 mutation), while the other patient had a small germline deletion within the hMLH1 gene (26). These data thus contradicted the twohit model generally believed to explain the biochemical and biological features of HNPCC patients. The basis for this MMR deficiency in the normal cells of these patients was unclear, and several potential explanations were offered. For example, it was possible that the second allele of the relevant MMR gene was inactivated in the germline of these patients through an undiscovered mechanism, or that unknown mutations of other genes involved in the MMR process were present that cooperated with the known germline mutation. It is clear from knockout experiments in mice that MMR deficiency is compatible with normal growth and development, supporting these possibilities (1,3,6). Alternatively, it was possible that the mutant alleles exerted a dominant negative effect, resulting in MMR deficiency even in the presence of the wildtype allele of the corresponding MMR gene and all other genes involved in the MMR process. To distinguish between these possibilities, we expressed the truncated polypeptide encoded by the hPMS2134 mutation in an MMR proficient cell line and analyzed its affect on the cell's MMR activity. The results showed that this mutant could indeed exert a dominant negative effect, resulting in biochemical and genetic manifestations of MMR deficiency.

The MMR proficient Syrian hamster TKts13 cell line (hereafter called SH cells) was cotransfected with various hPMS2 expression plasmids plus reporter constructs for assessing MMR activity. The hPMS2 expression plasmids contained the normal hPMS2 gene product or the truncated hPMS2 gene identified in the patient described above (PMS2WT and PMS2134, respectively, FIG. 1A). An "empty" vector devoid of hPMS2 sequences (PMS2NOT, FIG. 1A) served as an additional control. The reporter construct pCAROF (out of frame) contained a hygromycin resistance gene plus a β-galactosidase gene containing a 29 bp outofframe polyCA tract at the 5' end of its coding region. The reporter construct pCARIF (in frame) was identical except that the polyCA tract was 27 bp and therefore did not disrupt the β-galactosidase reading frame (FIG. 1B). The pCAROF reporter would not generate β-galactosidase activity unless a framerestoring mutation (i.e., insertion or deletion) arose following transfection.

Different transfection schemes were used to evaluate the effects of the PMS2134 mutation on SH cells. In the first scheme, the expression vectors plus the reporters were cotransfected together. Pools containing greater than 100 clones and individual clones were generated following selection with hygromycin for 17 days and harvested for Western blot and β-galactosidase assays. SH cells transduced with PMS2WT and PMS2134 synthesized polypeptides of the expected size, as assessed with antihPMS2 antibodies on Western blots (FIGS. 2A and 2B). As expected, virtually no β-galactosidase activity was observed in SH cells transfected with the pCAROF reporter plus PMS2NOT (FIG. 2C). However, SH cells transfected with PMS2134 expressed considerable β-galactosidase activity, significantly more than those transfected with PMS2WT (FIG. 2C). These results suggested that the truncated polypeptide encoded by the PMS2134 construct perturbs the endogenous MMR machinery, resulting in deletions or insertions that restored the reading frame. The exact nature of these presumed deletions or insertions could not be assessed, as multiple copies of the reporter constructs were transduced under our conditions, and the wild type β-galactosidase sequence was in great excess over the expected mutants, precluding their demonstration by direct sequencing.

Figure 3B:
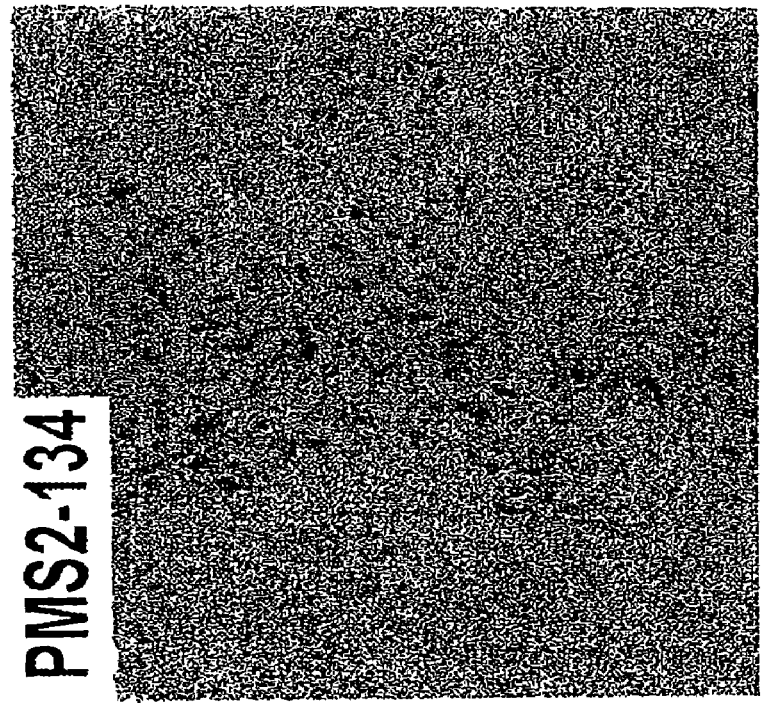
FIGS. 3A and 3B. In situ β-galactosidase activity of pooled clones of SH cells stably transduced with the PMS2WT (FIG. 3A), or PMS2134 (FIG. 3B) expression vectors, then retransfected with pCAROF reporter. After 17 days of drug selection, the colonies were pooled, cultured, and stained for β-galactosidase activity. A pooled culture of PMS2134 transduced SH cells expressing β-galactosidase from pCAROF is visible in FIG. 3B. Each of the fields illustrated is representative of that found in triplicate experiments.
Figure 3A:
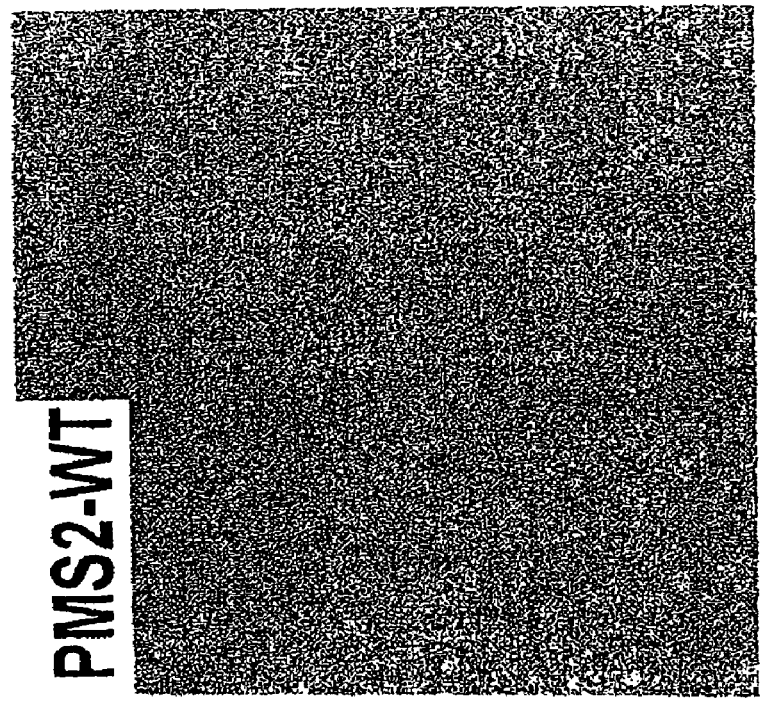

In the second scheme, SH cells were cotransfected with each of the PMS2 expression vectors plus the hygromycin resistance plasmid pLHL4. Hygromycin resistant cultures containing greater than 100 clones were pooled and expanded. These cultures were then cotransfected with pCARIF or pCAROF reporters plus a separate plasmid allowing geneticin selection. Two weeks later, the pooled cells, each containing more than 100 colonies resistant to both hygromycin and geneticin, were stained with Xgal to assess β-galactosidase activity. As shown in FIG. 3, the cultures transfected with PMS2134 (panel B) contained many blue cells, while virtually no cells were blue in the cultures transfected with PMS2WT (panels A). In each case, transfection efficiency was controlled by parallel transfections using pCARIF, which also served as a control for β-galactosidase activity of cells expressing the various PMS2 effector genes, which resulted in similar β-galactosidase expression levels in all cases (not shown). Increases in β-galactosidase activity after PMS2134 transfection compared to PMS2WT transfection were also observed when a similar experimental protocol was applied to the MMRproficient human embryonic kidney cell line 293. These cells were cotransfected with the pCAROF plus the various PMS2 effector plasmids and selected for 17 days in hygromycin. At day 17, colonies were stained with Xgal to assess β-galactosidase activity and scored for β-galactosidase expressing cells. As shown in Table 1, only those cells expressing the PMS2134 polypeptide expressed a detectable β-galactosidase activity. These data demonstrate a similar dominant negative effect of the hPMS2134 protein in both rodent and human systems and validate the utility of the rodent system in these studies.

TABLE 1

β-galactosidase expression of 293 clones transfected with pCAROF reporter construct plus PMS2 effector plasmids. 293 cells were cotransfected with the pCAROF β-galactosidase reporter plasmid plus the PMS2NOT, WT, or -134 effector plasmids. Transfected cells were selected in hygromycin for 17 days and stained with xgal for β-galactosidase activity (blue colored cells). The results below represent the mean +/ standard deviation of triplicate experiments.

| Sample | Blue colonies | White colonies |
| --- | --- | --- |
| PMS2NOT | 0 +/ 0 | 17 +/ 2.7 |
| PMS2WT | 0 +/ 0 | 18 +/ 4.0 |
| PMS2134 | 15 +/ 2.1 | 6 +/ 2.1 |

Plasmids. The fulllength wildtype hPMS2 cDNA was obtained from a human HeLa cDNA library as described (18). An hPMS2 cDNA containing a termination codon at amino acid 134 was obtained via RTPCR from the patient in which the mutation was discovered (9). The cDNA fragments were cloned into the BamHI site into the pSG5 vector, which contains an SV40 promoter followed by an SV40 polyadenylation signal (8). The pCAR reporter vectors described in FIG. 1 were constructed as described in ref. 21 and 25.

Cell lines and transfection. Syrian Hamster fibroblast Tkts13 and Human HEK293 cells were obtained from ATCC and cultured as described (15). Stably transfected cell lines expressing hPMS2 were created by cotransfection of the PMS2 expression vectors and the pLHL4 plasmid encoding the hygromycin resistance gene at a ratio of 3:1 (pCAR: pLHL4) and selected with hygromycin. Stably transfected cell lines containing pCAR reporters were generated by cotransfection of pCAR vectors together with either pNTK plasmid encoding the neomycin resistance plasmid or with pLHL4. All transfections were performed using calcium phosphate as previously described (15).

β-galactosidase assay. Seventeen days following transfection with pCAR, β-galactosidase assays were performed using 20 g of protein in 45 mM 2mercaptoethanol, 1 mM $MgCl_2$, 0.1 M $NaPO_4$ and 0.6 mg/ml Chlorophenol red β-D-galatopyranoside (CPRG, Boehringer Mannheim). Reactions were incubated for 1 hour, terminated by the addition of 0.5 M $Na_2CO_3$, and analyzed by spectrophotometry at 576 nm (16). For in situ β-galactosidase staining, cells were fixed in 1% glutaraldehyde in PBS and incubated in 0.15 M NaCl, 1 mM $MgCl_2$, 3.3 mM $K_4Fe(CN)_6$, 3.3 mM $K_3Fe(CN)_6$, 0.2% XGal for 2 hours at 37° C.

Western Blot.

Western blots for PMS2 were performed as described in example 5 using a polyclonal anti-human PMS2 raised against the codons 1-20 of the human full-length polypeptide.

activity, resulting in a higher frequency of mutation within the pCAROF reporter and reestablishing the ORF. To directly test the hypothesis that MMR was altered, we employed a biochemical assay for MMR with individual clones from cells containing the PMS2-WT, PMS2-134 or PMS2-NOT empty vectors as described in example 1. Nuclear extracts were prepared from the clones and incubated with heteroduplex substrates containing either a /CA\ insertiondeletion or a G/T mismatch under conditions described previously. The /CA\ and G/T heteroduplexes were used to test repair from the 3' and 5' directions, respectively. There was a dramatic difference between the PMS2-134 expressing clones and the other clones in these assays (Table 2A). While all clones repaired substrates from the 3' direction (/CA\heteroduplex), cells expressing the PMS2134 polypeptide had very little 5' repair activity. A similar directional defect in mismatch repair was evident with pooled clones resulting from PMS2134 transfection, or when the heteroduplex contained a 24 base pair loop, examples of which are shown in Table 2B. A small decrease in MMR activity was observed in the 3'/CA\PMS2-WT repair assays, perhaps a result of interference in the biochemical assays by over expression of the PMS2 protein. No significant activity was caused by PMS2-WT in the in situ β-galactosidase assays (FIG. 3; Table 1), a result more likely to reflect the in vivo condition.

TABLE 2

Mismatch repair activity of nuclear extracts from SH clones (A) or pooled cultures (B). The extracts were tested for MMR activity with 24 fmol of heteroduplex.

A. SH clones*

| Cell Line | Repaired substrate (fmol/15 min) | |
|---|---|---|
| | 3'/CA\ | 5'G/T |
| PMS2-NOT | | |
| clone A | 10.2 | 3.5 |
| clone B | 12.7 | 2.9 |
| clone C | 13.5 | 5.5 |
| PMS2-WT | | |
| clone A | 2.8 | 2.2 |
| clone B | 5.7 | 4.8 |
| clone C | 4.7 | 2.9 |
| PMS2-134 | | |
| clone A | 2.5 | 0.0 |
| clone B | 2.4 | 0.0 |
| clone C | 5.0 | 0.5 |

B. Pooled cultures

| Cell Line | Repaired substrate (fmol/15 min) | | | |
|---|---|---|---|---|
| | 3'G/T | 5'G/T | 3'/CTG\ | 5'/CTG\ |
| PMS2-NOT | 2.07 +/− 0.09 | 2.37 +/− 0.37 | 3.45 +/− 1.35 | 2.77 +/− 1.37 |
| PMS2-WT | 1.65 +/− 0.94 | 1.86 +/− 0.57 | 1.13 +/− 0.23 | 1.23 +/− 0.65 |
| PMS2-134 | 0.14 +/− 0.2 | 0.0 +/− 0.0 | 1.31 +/− 0.66 | 0.0 +/− 0.0 |

*These data represent similar results derived from greater than five independent experiments.

EXAMPLE 2

Dominant Negative Mismatch Repair Gene Alleles Cause a Defect in MMR Activity

The most likely explanation for the differences in β-galactosidase activity between PMS2WT and PMS2134 transfected cells was that the PMS2134 protein disturbed MMR Biochemical assays for mismatch repair. MMR activity in nuclear extracts was performed as described, using 24 fmol of substrate (12,25). Complementation assays were done by adding~100 ng of purified MutL α or MutSα components to 100 µg of nuclear extract, adjusting the final KCl concentration to 100 mM (4,10,30). The substrates used in these experiments contain a strand break 181 nucleotides 5' or 125 nucleotides 3' to the mismatch. Values represent experiments performed at least in duplicate.

EXAMPLE 3

Use of MMR Defective Cells and Chemical Mutagens to Enhance Mutations in Genetic Loci To enhance the rate of genetic mutations and produce cells with altered genes, RNA expression, or polypeptides, the use of MMR deficiency and chemical mutagens is a powerful tool to generate such diversity. The advantages of using MMR defective cells is that the decrease of this activity renders cells more resistant to the toxic effects of such compounds yet allows for the increase in genetic and phenotypic alterations of a host organism or cell. The following experiments are performed to demonstrate the utility of the invention. Cells that are genetically defective for MMR such as but not limited to HCT116, DLD-1, etc. or cells such as those described in example 1 and 2 that are made MMR defective by ectopic expression of a dominant negative allele is covered under this invention. Briefly, MMR proficient and deficient cells are incubated with a range (1 nm to 1 mM) of chemical mutagens for 1 hour to 24 hours at 37 C. at 5% $CO_2$ in growth medium. After incubation is complete, chemical mutagens are washed from medium and cells are grown in the presence of hypoxanthine, aminopterin, and thymine to score for HPRT mutant cells as previously described (Walker, V E et.al. Mutat Res. 17:371-388, 1999.) and known to those skilled in the art. Cells are plated at $1 \times 10^5$ cell ml in 10 cm tissue culture dishes and grown for 14 days at 37 C. at 5% $CO_2$ in growth medium. After 14 days, the numbers of HAT-resistant colonies are determined by counting under the microscope. A typical experiment will demonstrate that a significantly greater number of HAT resistant colonies (due to altered HPRT gene) are formed in chemically treated MMR defective cells than in control cells, demonstrating the ability to increase mutations within an endogenous gene of the host cell/organism. The use of MMR defective cells plus exposure to chemical or ionizing radiation can also be used to enhance genetic mutation in vivo within target genes introduced via transfection and screening of transient or stable cell lines. In order to demonstrate the ability of MMR deficiency plus chemical mutagens to enhance genetic mutation within a transduced target gene, we employed the use of cells described above, whereby the pCAROF vector (see EXAMPLE 1) was transfected into HCT116 cells. Cells were selected for pCAR-OF positive clones via hygromycin resistance. Hygromycin-resistant cells were grown to confluence and 100,000 cells were exposed to 10 µM ethylmethane-sulfonate (EMS) alkylating compound for 8 hours and returned to growth medium. Cells were then grown overnight and then plated at a density of 1,000 cells plate in 10 cm dishes in triplicate. Cells were grown for 10 days and scored for β-gal activity using methods described in EXAMPLE 1. The results showed that cells grown in the absence of the compound the number of β-gal positive foci were 92+/−10 per dish. In contrast, cells exposed to EMS resulted in a significant increase in the number of β-gal positive cells (205+/−18). These data demonstrate the use of MMR defective cells plus chemical mutagens to generate genetic mutations in target genes in vivo. This method is useful for generating genetic diversity in target genes for commercial purposes.

EXAMPLE 4

Restored DNA Stability of a Mismatch Repair Deficient Cell Expressing a Dominant Negative MMR Gene Allele by Inducible Vector The ability to induce DNA hypermutability using ectopic expression of a dominant negative MMR gene allele has many important commercial applications for generating eucaryotic cells with genetically diverse subtypes. The following experiments demonstrate the ability to permanently imprint a genetic change in the genome of a MMR defective cell as described in Examples 1 and 2 by restoring its MMR proficiency. First, the PMS2-134 dominant negative allele was cloned into the eucaryotic inducible vector systems pcDNA4/TO (tetracycline-inducible vector) (Invitrogen), referred to as pcDNA4/TO/PMS134S, the pIND/V5-His glucocorticoid inducible vector (Invitrogen), referred to as pIND/PMS134S. Tk-ts13 or HEK293 cells were cotransfected with each vector plus the pCAR-OF (contains hygromycin-resistance gene as selectable marker) as described below. An empty vector was used as control for each combination. Transfected cells were selected for 10-14 days for zeocin/hygromycin (Z/H) or neomycin/hygromycin (N/H) resistant cells. Clones were picked and expanded as individual clones or pools. Cells were expanded and plated in 6-well tissue culture plates at $1 \times 10^5$ cell/ml in growth medium (DMEM plus 10% fetal bovine serum) with or without inducer chemicals (1 µg/ml of tetracycline for pcDNA4/TO/PMS134S and 1 µM ecdysone for pIND/PMS134S). Cell cultures were harvested and analyzed for PMS2-134 induced protein expression via western (as described in example 5) after 24 hours of culture at 37° C. in 5% $CO_2$. Western analysis of extracts of PIND/PMS134S cells revealed production of a protein of~17 kd when grown in the presence of ecdysone, while those grown without ecdysone had no detectable levels. Clones that have inducible PMS2-134 expression were expanded and grown in the presence of ecdysone or tetracycline for 24 hours. Cells were harvested for 72 hours to identify the kinetics of loss of PMS2-134 expression via western blot in the absence of inducer. These data demonstrated undetectable levels of proetin ater 72 hours.

Figure 5:
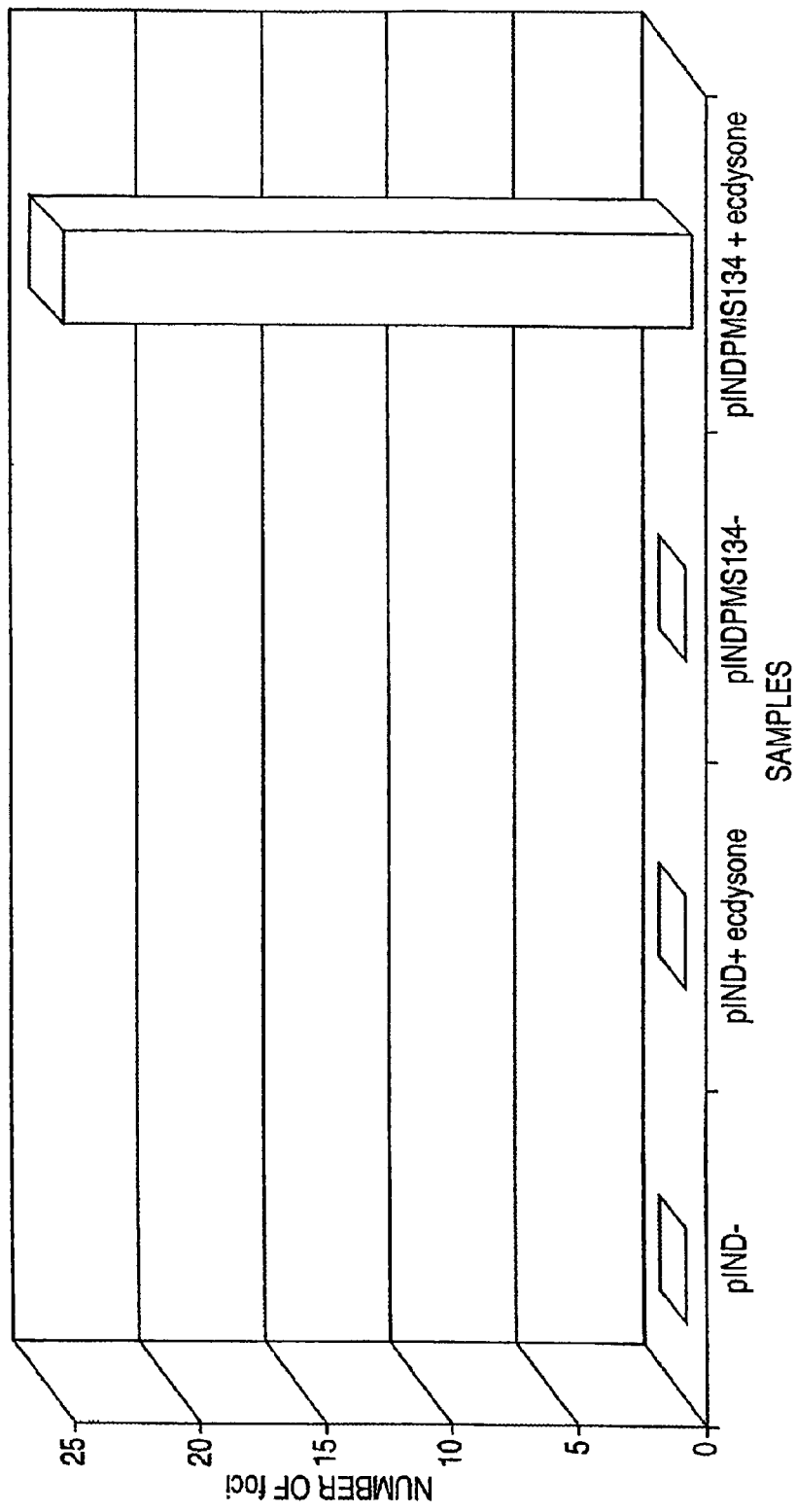
FIG. 5. Generation of altered gene sequences upon induction of PMS134. Cells containing pIND empty vector or pINDPMS134 were transfected with the pCAR-OF plasmid containing the β-galactosidase reporter plasmid with a polyCA repeat in the N-terminus of the β-gal gene, which disrupts the open reading frame to produce a frameshift. The plasmid also contains the hygromycin resistance gene to select for stable lines. Cells that were G418/hygromycin resistant were expanded and grown for 10 days with or without 1 μM ecdysone. At day 14, cells were stained in situ for foci that produced functional β-gal. As shown, a significant number (25/field) of β-gal positive foci were observed in cells grown in the presence of the steroid inducer while little were observed in cultures grown without the inducer molecule.
Figure 6:
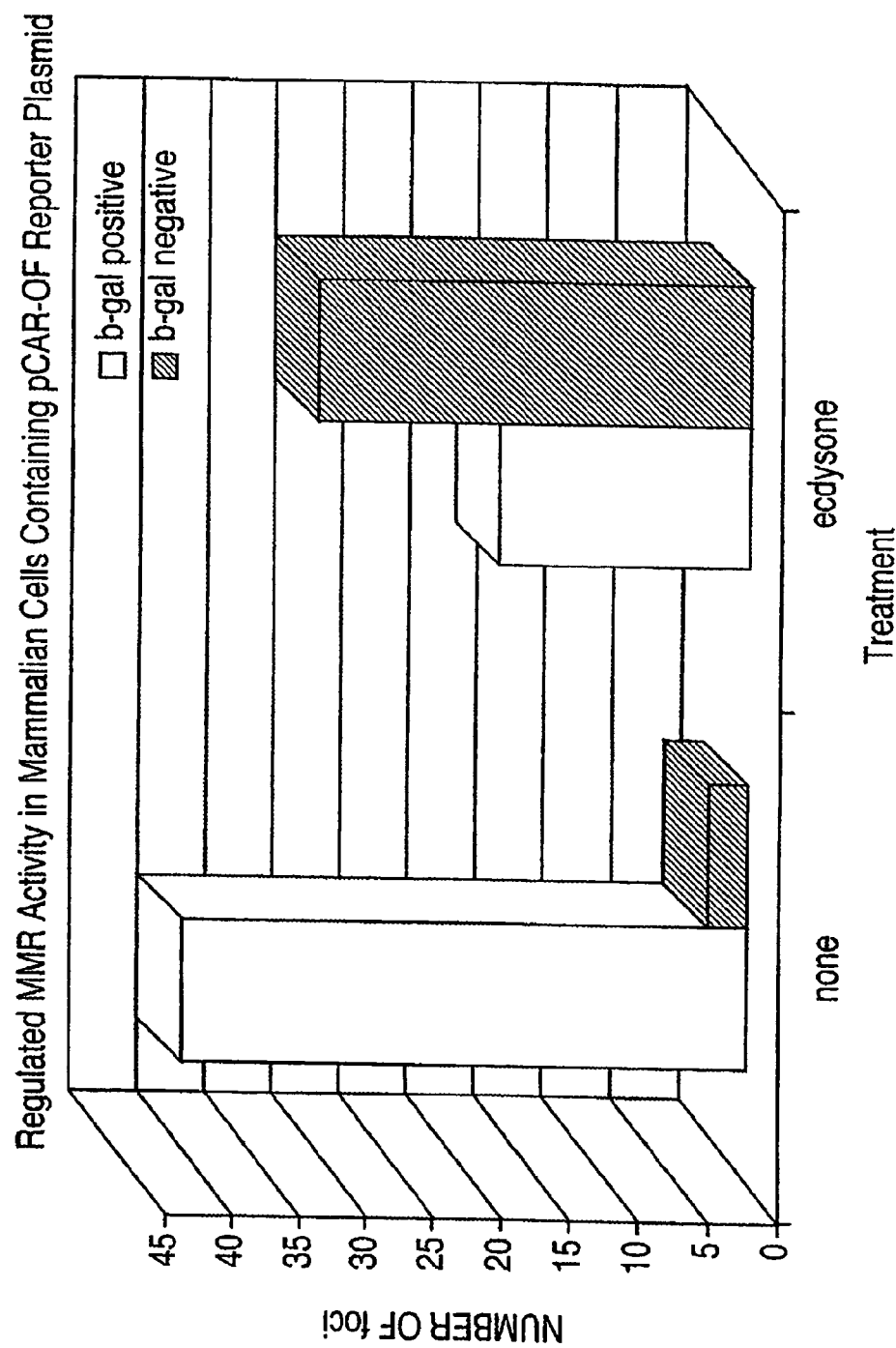
FIG. 6. Re-establishment of genetically stable cells after selection. To determine if clones were genetically stable after removal of chemical inducer (and subsequent shut down of dominant negative MMR allele), pINDPMS134/pCAR-OF clones were isolated and tested for functional β-gal activity. Clones with β-gal expression were plated in 96 well plates at limiting dilution yielding roughly 45 well with clones per dish. Clones were again grown 14 generations (1 generation/day) with or without ecdysone and stained for β-gal activity in situ. As shown, a significant number of β-gal positive clones were observed in cells grown in the absence of the steroid inducer (42/45 wells were positive for β-gal) while a larger number of clones lost β-gal activity under constant inducer exposure (18/45 wells were positive for β-gal). These data demonstrate the ability to restore genetic stability in clones that have been genetically altered in vivo via blockade of MMR.

To demonstrate the ability to induce genetic instability using an inducible vector system, cells containing the pIND/PMS134S or pIND/V5-His were grown for 14 days with or without ecdysone and stained to measure β-gal activity in situ as described (MCB paper). As shown in FIG. 5, a significant number of cellular foci stained positive blue in pIND/PMS134S cells grown in the presence of ecdysone (25 cells/field as observed under inverted microscopic evaluation) in contrast to empty vector controls which had no observable blue foci. In contrast, neither the pIND/PMS134S nor the pIND/V5-His cells grown in the absence of the inducer stained positive. These data demonstrate the ability of using dominant negative MMR genes under control of inducible vectors to generate genomic instability and genetic diversity in genes to produce altered biochemical functions and/or new phenotypes.

To demonstrate that suppressing PMS2-134 expression can restore MMR proficiency in these cells, the following experiment was performed. Cells were maintained in inducer medium plus Z/H or N/H for 14 days. A subset of each clone or pool was plated into 24-well falcon dishes at $5 \times 10^4$ cell/ml. Cells were grown overnight at 37° C. in 5% $CO_2$. The next day, cells were stained in vivo for β-galactosidase expression as previously described (Nicolaides et.al. Mol. Cell Biol. 18:1635-1641, 1998). Cells that turn blue have done so because of a decrease in their endogenous MMR activity due to the dominant negative effects of PMS2-134 on the MMR machinery. These cells were subcloned by limiting dilution in 96 well plates in the presence or absence of inducer molecule. Restored genetic stability was demonstrated in the PMS2-134 expressing clones when a lower number of revertants (non-blue cells) were found in the clones where the inducer agent was removed (42 out of 45 wells in contrast to plates where clones were under constant exposure to inducer (18 out of 45 wells)). These data demonstrate the ability to regulate genomic stability and genetic evolution using regulated MMR gene expression.

The use of chemical mutagens as described EXAMPLE 3 in combination with the inducible MMR gene strategy described above are also taught in the application as a method for generating genetically diverse host organisms with new phenotypes and/or for stable production of altered gene expression. To demonstrate this effect, cells containing inducible dominant negative expression are exposed to inducer molecule and subsequently exposed to chemical mutagen or ionizing radiation. Cells are then expanded in the presence of inducer molecule and cultures are selected for cells with new phenotypes and/or altered gene structure as determined by sequence analysis or biochemical activity. Cells with altered gene or phenotype are then removed from inducer molecule and genetic stability and phenotype are restored.

Transfections

Generation of stable HEK293 cells containing the ecdysone receptor with the pIND/PMS134S or pcDNA/TO/PMS134S inducible vector. HEK293-ecdysoneR cells were transfected with the pIND or pcDNA/TO empty vector or the pIND/PMS134S or pcDNA/TO/PMS134S vector using Lipofectamine 2000 (Gibco/BRL). Cells were selected for selectable marker resistance and clones and pools were expanded. Stable lines were then exposed to 1 µM ecdysone for 48 hours and extracts were isolated and analyzed by western blot to identify clones with induced PMS134 expression using antiserum directed to the N-terminus of the PMS134 polypeptide as described below.

Plasmids

Figure 4:
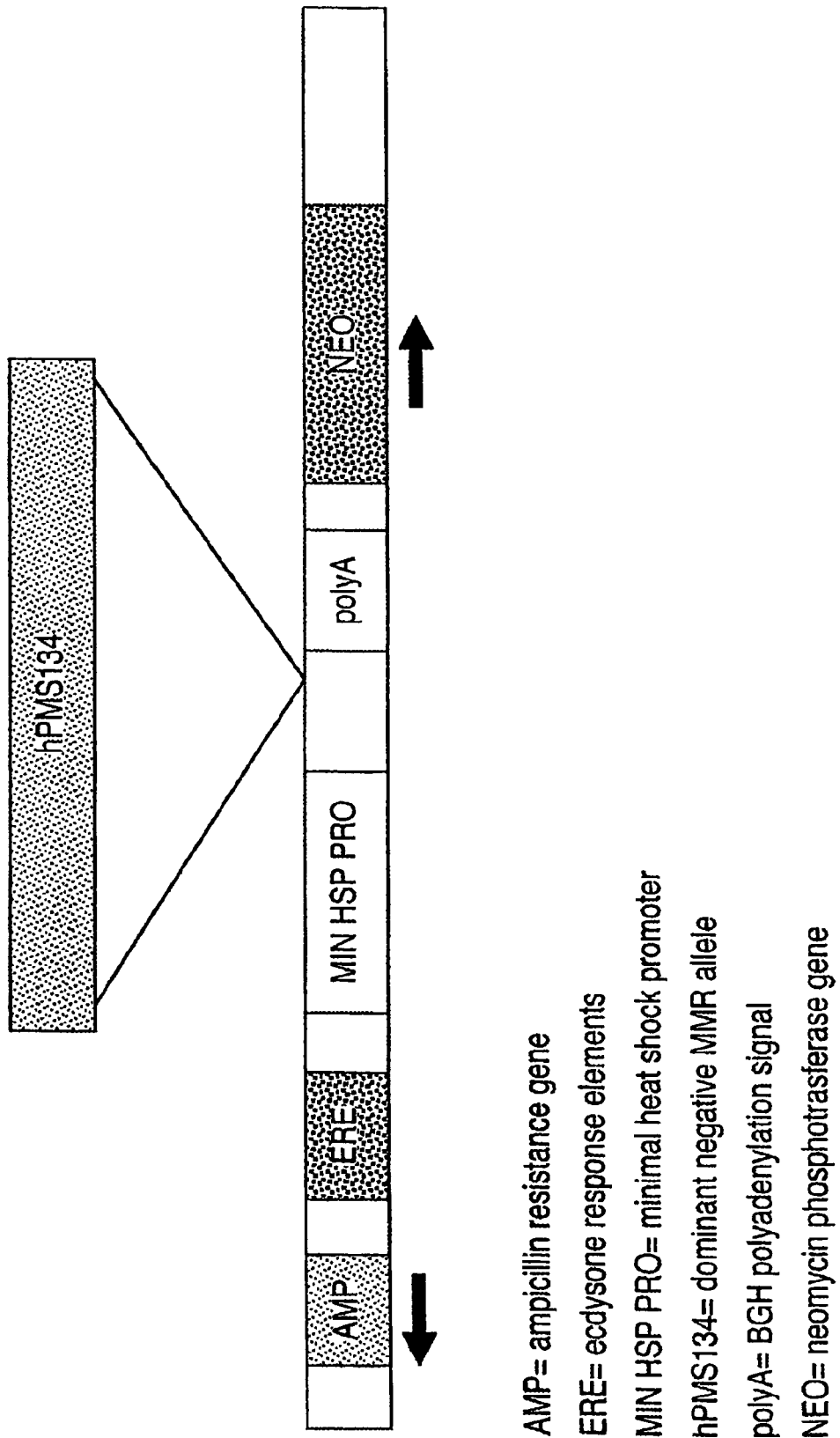
FIG. 4. Generation of inducible mammalian expression vectors containing dominant negative mismatch repair gene alleles. The PMS134 cDNA with or without a V5 epitope at the C-terminus was cloned into the ecdysone-steroid regulated pIND mammalian expression vector. The PMS134 cDNA was cloned into the unique BamHI site of the vector in the sense orientation to the Heat shock Minimal Promoter. The resultant vectors are referred to as pINDPMS134V5 or pINDPMS134, respectively. The pIND vector contains that neomycin resistance gene as selectable marker.

The PMS2-134 was cloned as a BamHI fragment from the pSG5PMS134 (described in example 1) vector into the following inducible expression vectors. The tetracycline inducible vector (pcDNA4/TO/PMS134S) contains the zeocin selectable marker under control of the EM-7 promoter and SV40 polyA sequences. The structure of the plasmid was confirmed by endonuclease restriction analysis and sequencing. The glucocorticoid inducible vector (pIND/PMS134S) contains the neomycin selectable marker under control of the SV40 early promoter and polyA sequences. A schematic figure of the vector is presented in FIG. 4.

Transfections

Inducible expression vectors were co-transfected into Tk-ts13 cells and HEK293 cells following the methods described above either alone or in combination with the pCAR-OF vector as described in EXAMPLE 1. Cells were selected for zeocin/hygromycin (pcDNA4/TO/PMS134S) or neomycin/hygromycin (pIND/PMS134S) resistant clones as described (ref 15, Grasso et.al. J. Biol. Chem. 273:24016-24024, 1998). Resistant clones are picked and/or pooled and expanded for protein analysis.

EXAMPLE 5

Figure 8A:
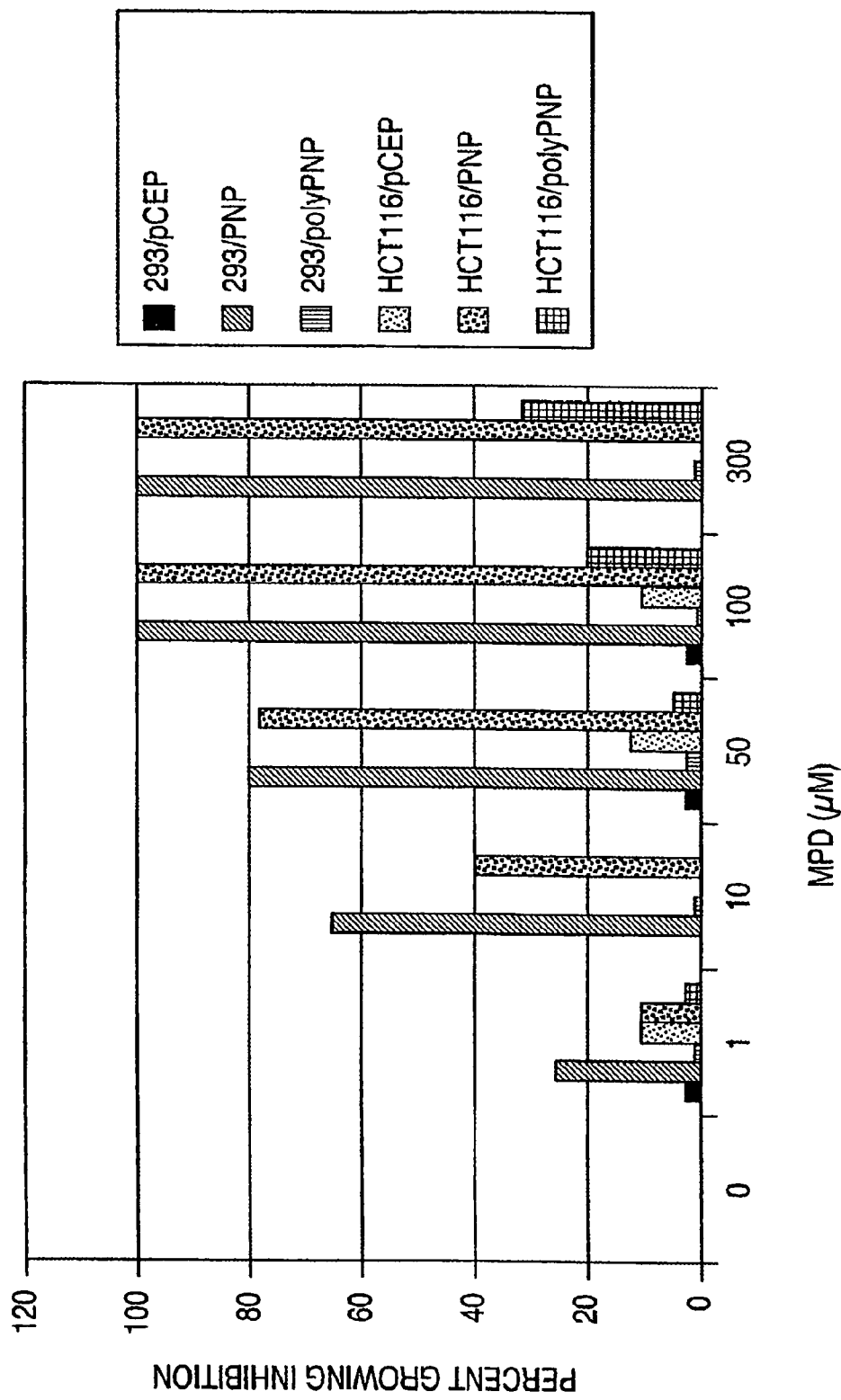

Restoration of MMR and Restoration of a Genetic Stability by Expressing a MMR Gene Complementing Gene and Establishment of a Fixed Genomic Structure The use of cells with defective MMR repair due to defects of endogenous genes such as but not limited to the HCT116, DLD-1, and HEC-1-A cells lines (ref. 12, 25 and Kondo, et.al. J Biochem 125:818-825, 1999) can be useful for altering the genetic structure of genes to produce commercially viable variant molecules such as novel anti-microbial agents, bioactive growth factors or hormones, altered antibody structures, etc. The utility and value of such a cell is that once an altered gene structure has been produced, the integrity of this gene alteration can be preserved in the cell's genome by making the cell genetically stable via the introduction of a functional complementing MMR gene. This example demonstrates that the introduction of a genetically altered bacterial purine nucleotide phosphorlyase (PNP) gene, where an out-of-frame poly-A tract is inserted at the N-terminus of the gene (referred to as polyPNP), can be genetically altered in a MMR deficient cell and also be genetically stable when a MMR defective cell is made MMR proficient by the direct expression of a complementing MMR gene. The polyPNP gene encodes for a non-functional PNP gene. When the poly-A tract is randomly altered by genetic alterations due to defective MMR, the tract is randomly altered, allowing for the production of a functional PNP gene and polypeptide. PNP converts the non-toxic 9-(β-D-2-deoxy-erythro-pento-furanosyl)-6-methyl-purine prodrug (referred to as MPD) substrate to the toxic 6-methyl purine analog (referred to as MP) (Sorscher, E J, et.al. Gene Therapy 1:233-238, 1994). The polyPNP gene was engineered to contain a hemaglutinin epitope tag at the C-terminus to facilitate the detection of the encoded polypeptide via western blot analysis using an anti-HA antibody. The polyPNP gene was cloned into the pCEP4 expression vector, which has a hygromycin resistance (Hyg) gene for selection. The schematic diagram showing this gene is given in FIG. 7. A homologous gene called PNP was also made in which an in-frame polyA tract is cloned into the N-terminus of the gene as a positive control for PNP activity. Briefly, the MMR defective HCT116 cell line and the MMR proficient HEK293 cell line were transfected with the polyPNP, the PNP expression vector, or an empty pCEP4 vector. Cells were then selected for Hyg resistance and clones were isolated. Expanded cells were grown in the presence of increasing amounts of MPD (0, 1, 10, 50, 100, 300 µM) for 10 days. After treatment period, cells were counted by hemocytometer and trypan blue exclusion. As shown in FIG. 8A, a 20% and 30% decrease in cell numbers were observed when HCT116/polyPNP cells were cultured in the presence of 100, µM or 300 µM MPD, respectively. In contrast no decrease in cell growth was observed with the MMR proficient HEK293/polyPNP cells even at the highest concentration (300 µM) of MPD used. For both cell lines, the expression of PNP resulted in 100% growth suppression when cells were grown in the presence of 50-300 µM MPD, demonstrating the toxic effects of the converted MP on both cell lines. Western blot confirmed that a polypeptide containing the HA epitope was indeed produced in the HCT116/polyPNP cells, thus demonstrating that that the polyPNP gene structure was altered to produce a functional and full-length PNP enzyme (FIG. 8B).

Figure 9:
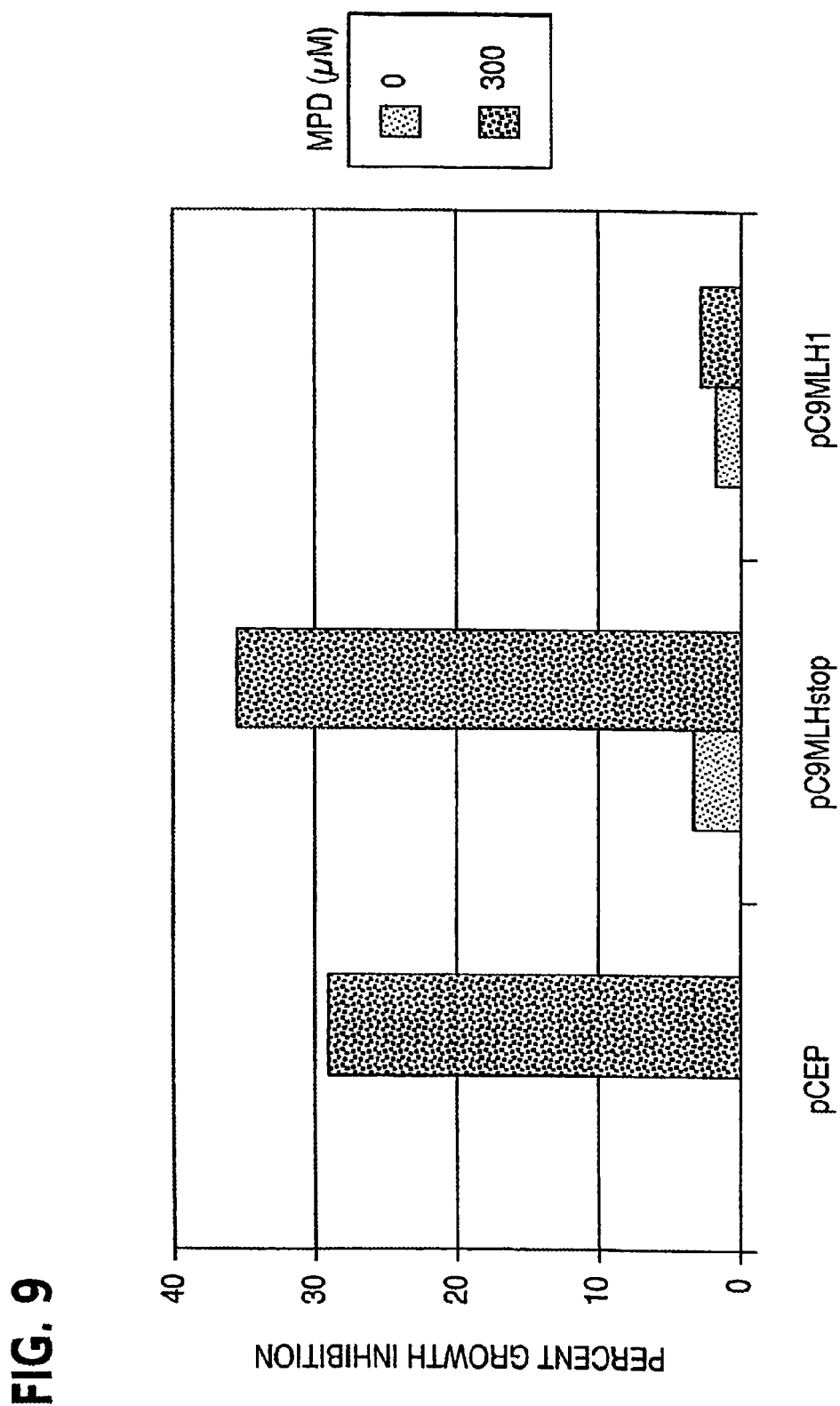
FIG. 9. Toxicity assay of a MMR defective or proficient cell line expressing polyPNP with or without exposure to MPD. The graph shows that in MMR-defective HCT116 cells (genetically deficient for MLH1), the introduction of a functional MLH1 gene restores the genetic stability of the cell as indicated by the fact that the polyPNP gene is not converted to an active form as seen in HCT116 cells transfected with a truncated (non-functional) MLH1 cDNA (pC9MLHstop). These data demonstrate that MMR deficiency can be complemented with a functional MMR gene (HCT116/pC9MLH1), therefore maintaining the genomic integrity of a gene or locus that has been altered.
Figure 10B:
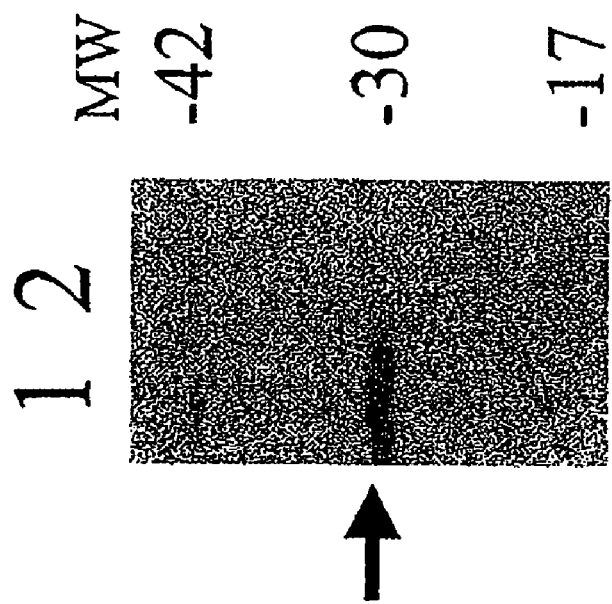
FIGS. 10A and 10B. Western blot of cells transfected with an MLH1 expression construct and the polyPNP gene.
Figure 10A:
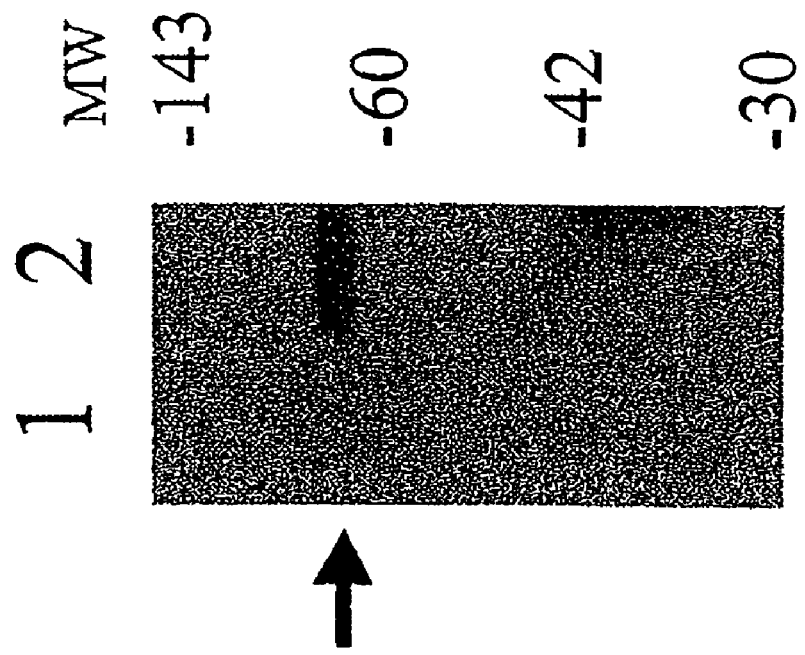

The restoration of genetic stability and the subsequent imprint of an altered gene locus or loci is an important invention of this application for producing viable biological products, whereby altered biomolecules, cells or whole organisms with desired altered output traits are made genetically stable for long term use. To generate stable MMR defective cell lines that has or has not been exposed to chemical mutagens and selected for desired genetic changes, the introduction of a complementing MMR gene that can substitute for the mutated endogenous MMR gene locus is taught in this application. This is demonstrated by the example using HCT116 cells, which are genetically deficient for the human MutL homolog MLH1 (12, 24, 25). In this example, a mammalian expression vector is used that encodes for the functional MLH1 polypeptide (pC9MLH1) or an expression vector that encodes for a MLH1 cDNA with a premature stop codon (pC9MLHstop). These expression vectors contain a neomycin (neo) resistance gene that allows for selection of cells containing this vector. To demonstrate the ability of complementing MMR activity in an otherwise MMR defective cell and to permanently imprint the altered structure(s) of a gene locus, the polyPNP and pC9MLH constructs were cotransfected into HCT116 cells. Cells were selected for 10 days in neo and Hyg and resistant clones were isolated and expanded. Cells were then cultured in the presence of MPD and counted for growth after 10 days. As demonstrated in FIG. 9, cells transfected with the MLH1 wild type cDNA expressed MLH1 as determined by western, in contrast to cells transfected with MLHstop. In addition, when cells were grown in the presence of 300 µM MPD, those cells expressing MLH1 showed a 2% decrease in total cell growth as compared to cells grown in medium alone, while cells transfected with the MLHstop or empty vector and polyPNP had a 35% reduction in cell growth in comparison to cells grown in medium alone. These data demonstrate that complementing the MMR defect with an ectopically expressed wild type MMR gene or cDNA can establish genomic stability of a MMR defective cell line and establish long term stable lines that have been selected for to produce new output traits and/or modified genomic or polypeptide structures, such as biologically active or inactive PNP.

Plasmids.

The fulllength wildtype hMLH1 cDNA was obtained from a human Hela cDNA library as described (18). A MLH1 cDNA containing a termination codon was obtained via RTPCR from the patient in which the mutation was discovered (24). The cDNA fragments were cloned into the XhoI site of the pCEP9 vector (Invitrogen), which contains CMV promoter followed by an SV40 polyadenylation signal (8) and a gene, which encodes for neomycin resistance. The pC9MLH1 vector produces the full-length function MLH1 protein, while the pC9MLH1 stop produces the non-functional truncated MLH1 polypeptide. The polyPNP and PNP vectors are described in FIG. 4. The polyPNP contains a 21 base out-of-frame polyA tract inserted after codon 2 of the bacterial PNP gene which results in a truncated polypeptide (Sorscher, E J, et.al. Gene Therapy 1:233-238, 1994). The polyPNP contains a 20 base in-frame polyA tract inserted after codon 2 of the bacterial PNP gene which results in a full-length functionally active PNP protein. Both the polyPNP and PNP gene have a hemaglutinin (HA) epitope fused in-frame at the C-terminus followed by a termination codon. The polyPNP and the PNP gene was constructed by polymerase chain reaction using a sense primer: 5'-ccaagcttagaccaccatggc aaaaaaaaaaaaaaaaaaaaaatcgctaccccacacattaatgc-3' (SEQ ID NO: 1), where the polyA tract is underlined while the primer for PNP contains 1 less A in the polyA tract. The antisense primer for both constructs is 5'-ataagaatgcggccgctatcct-tagctagcgtaatctggaacatcg-taagcgtaatctggaacatcgtactctttatcgcccagcag-3' (SEQ ID NO: 2). DH5α bacterial DNA was used a template for amplification. The modified PNP gene was produced by amplification USING 95° C. FOR 30 SEC, 54° C. FOR 1 MINUTE, 72° C. for 1 min for 25 cycles in buffers as previously described (19). Amplified genomic inserts were cloned into T-tailed vectors (TA cloning, Invitrogen) and recombinant clones were sequenced to identify vectors with correct nucleotide sequences. PNP fragments were then subcloned into the KpnI-XhoI sites of the pCEP4 vector (Invitrogen) using sites from the TA cloning vector polylinker. Recombinant PNP expression vectors were sequenced to ensure sequence authenticity using internal primer sequences.

Cell Lines and Transfection

Human HCT116 and HEK293 cells were obtained from ATCC and cultured as suggested by the vendor in RPMI plus 10% fetal bovine serum. Cells were transfected with PNP and/or MLH1 expression vectors using liposomes following the manufacturer's protocol (Gibco/BRL). Stably transfected cell lines were generated that express empty vector, PNP or polyPNP by transfection followed by hygromycin selection. For complementation experiments, HCT116 cells were transfected with PNP/MLH1, PNP/MLH1 stop, polyPNP/MLH1 or polyPNP/MLH1 stop at a 1:1 ratio using 5 µg of each plasmid and cells were selected for hygromycin and neomycin resistance. After 10 days, drug-resistant colonies were observed and picked for analysis.

MPD Killing Assay

For MPD killing assay, cells were plated at $2 \times 10^4$ cell/ml and 1 ml aliquots were plated in 24-well costar tissue culture dishes. For killing assays, cells were plated in 0, 1, 10, 50, 100, and 300 µM MPD in triplicate. Cells were grown for 10 days trypsinized and counted on hemocytometer using trypan blue exclusion. Data are presented as a mean+/−SD for each study.

Western Blot

After counting equal cell numbers from each 0 µM MPD treated cell was lysed directly in sample buffer (60 mM Tris, pH 6.8, 2% SDS, 10% glycerol, 0.1 M 2-mercaptoethanol, 0.001% bromophenol blue) and boiled for 5 minutes. Protein lysates were separated by electrophoresis on 18% Tris-glycine gels (Novex). Gels were electroblotted onto Inmobilon-P (Millipore) in 48 mM Tris, 40 mM glycine, 0.0375% SDS, 20% methanol and blocked at room temperature for 1 hour in Tris-buffered saline plus 0.05% Tween-20 and 5% condensed milk. Filters were probed with monoclonal antibodies (αMLH14) generated against human MLH1 or Hemaglutinin (HA) (Boehringer Manheim) and a horseradish peroxidase conjugated rabbit anti-mouse secondary antibody, using chemiluminescence for detection (Pierce). Mouse IgG was used as control for all experiments to assess for non-specific antibody interactions of the primary antibody and ensure that the antiserum used were detecting expected proteins.

REFERENCES

1. Baker S. M., Bronner, C. E., Zhang, L., Plug, A. W., Robatez, M., Warren, G., Elliott, E. A., Yu, J., Ashley, T., Arnheim, N., Bradley, N., Flavell, R. A., and Liskay, R.

M. 1995. Male defective in the DNA mismatch repair gene PMS2 exhibit abnormal chromosome synapsis in meiosis. Cell 82:309-319.
2. Bronner, C. E., Baker, S. M., Morrison, P. T., Warren, G., Smith, L. G., Lescoe, M. K., Kane, M., Earabino, C., Lipford, J., Lindblom, A., Tannergard, P., Bollag, R. J., Godwin, A., R., Ward, D. C., Nordenskjold, M., Fishel, R., Kolodner, R., and Liskay, R. M. 1994. Mutation in the DNA mismatch repair gene homologue hMLH1 is associated with hereditary nonpolyposis colon cancer. Nature 368:258-261.
3. de Wind N., Dekker, M., Berns, A., Radman, M., and Riele, H. T. 1995. Inactivation of the mouse Msh2 gene results in mismatch repair deficiency, methylation tolerance, hyperrecombination, and predisposition to cancer. Cell 82:321-330.
4. Drummond, J. T., Li, G. M., Longley, M. J., and Modrich, P. 1995. Isolation of an hMSH2p160 heterodimer that restores mismatch repair to tumor cells. Science 268:1909-1912.
5. Drummond, J. T., Anthoney, A., Brown, R., and Modrich, P. 1996. Cisplatin and adriamycin resistance are associated with MutL□ and mismatch repair deficiency in an ovarian tumor cell line. J. Biol. Chem. 271:9645-9648.
6. Edelmann, W., Cohen, P. E., Kane, M., Lau, K., Morrow, B., Bennett, S., Umar, A., Kunkel, T., Cattoretti, G., Chagnatti, R., Pollard, J. W., Kolodner, R. D., and Kucherlapati, R. 1996. Meiotic pachytene arrest in MLH1 deficient mice. Cell 85:1125-1134.
7. Fishel, R., Lescoe, M., Rao, M. R. S., Copeland, N. J., Jenkins, N. A., Garber, J., Kane, M., and Kolodner, R. 1993. The human mutator gene homolog MSH2 and its association with hereditary nonpolyposis colon cancer. Cell 7:1027-1038.
8. Green, S., Issemann, I., and Sheer, E. 1988. A versatile in vivo eucaryotic expression vector for protein engineering. Nuc. Acid Res. 16:369.
9. Hamilton, S. R., Liu, B., Parsons, R., E., Papadopoulos, N., Jen, J., Powell, S. M., Krush, A. J., Berk, T., Cohen, Z., tetu, B., Kinzler, K. W., and Vogelstein, B. 1995. The molecular basis of Turcot's syndrome. N. Eng. J. Med. 332:839-847.
10. Holmes, J., Clark, S., and Modrich, P. Strand specific mismatch correction in nuclear extracts of human and *Drosophila melanogaster* cell lines. (1990). Proc. Natl. Acad. Sci. USA 87:5837-5841.
11. Leach, F. S., Nicolaides, N. C, Papadopoulos, N., Liu, B., Jen, J., Parsons, R., Peltomaki, P., Sistonen, P., Aaltonen, L. A., NystromLahti, M., Guan, X. Y., Zhang, J., Meltzer, P. S., Yu, J. W., Kao, F. T., Chen, D. J., Cerosaletti, K. M., Fournier, R. E. K., Todd, S., Lewis, T., Leach R. J., Naylor, S. L., Weissenbach, J., Mecklin, J. P., Jarvinen, J. A., Petersen, G. M., Hamilton, S. R., Green, J., Jass, J., Watson, P., Lynch, H. T., Trent, J. M., de la Chapelle, A., Kinzler, K. W., and Vogelstein, B. 1993. Mutations of a mutS homolog in hereditary nonpolyposis colorectal cancer. Cell 75:1215-1225.
12. Li, G. M., and Modrich, P. 1995. Restoration of mismatch repair to nuclear extracts of H6 colorectal tumor cells by a heterodimer of human mutL homologs. Proc. Natl. Acad. Sci. USA 92:1950-1954.
13. Liu, et al. 1996. Nat. Med. 2:169-174
14. Modrich, P. 1994. Science 266:1959-1960
15. Nicolaides, N. C. et al., 1991. Mol. Cell. Biol. 11:6166-6176
16. Nicolaides, N. C. et al., 1992. J. Biol. Chem. 267:19665-19672
17. Nicolaides N. C., et al., 1994. Nature 371:75-80
18. Nicolaides N. C., et al., 1995. Genomics 29:329-334
19. Nicolaides N. C., et al., 1995. Genomics 30:195-206.
20. Nicolaides N. C., et al., 1995. Genomics 31:395-397.
21. Palombo et al., 1994. Nature 36:417.
22. Palombo et al., 1995. Science 268:1912-1914.
23. Pang et al., 1997. Mol. Cell. Biol. 17:4465-4473.
24. Papadopoulos, N. et al., 1994. Science 263:1625-1629.
25. Parsons, R. et. al. 1993. Cell 75:1227-1236.
26. Parsons, R. et al. 1995. Science 268:738-740.
27. Perucho, M. 1996. Biol. Chem. 377:675-684.
28. Prolla, T. A. et al. 1994. Science 264:1091-1093.
29. Strand, M. et al., 1993. Nature 365:274-276.
30. Su et al., 1988. J. Biol. Chem. 263: 6829-6835.

We claim:

1. A method for generating a mutation in a gene of interest, comprising the steps of:
   growing in vitro under inducing conditions at least one mammalian cell comprising
   (a) a gene of interest and
   (b) a dominant negative allele of a mismatch repair gene under control of an inducible regulatory element, wherein the dominant negative allele of a mismatch repair gene encodes a polypeptide comprising the N-terminal 133 amino acids of PMS2;
   contacting the at least one cell with a mutagen; and
   testing the at least one cell to determine whether the gene of interest harbors a mutation that results in a detectable phenotype.

2. The method of claim 1 further comprising the step of: decreasing expression of the dominant negative allele in the selected one or more cells by culturing in non-inducing conditions.

3. The method of claim 1 wherein expression of the dominant negative allele is decreased by site directed mutagenesis of the dominant negative allele.

4. A method for generating a mutation in a gene of interest comprising the steps of:
   treating at least one cell in vitro with a mutagen, said at least one cell comprising (a) a gene of interest and (b) a dominant negative allele of a mismatch repair gene operably linked to a promoter, wherein the dominant negative allele of a mismatch repair gene encodes a polypeptide comprising the N-terminal 133 amino acids of PMS2; and
   testing the at least one cell to determine whether the gene of interest harbors a mutation that results in a detectable phenotype.

5. The method of claim 4 further comprising the step of: introducing a complementing mismatch repair gene into the one or more selected cells whereby genetic stability is restored.

6. The method of claim 5 where the complementing mismatch repair gene is constitutively active in the one or more selected cells.

7. The method of claim 5 wherein the complementing mismatch repair gene is inducibly regulated.

8. The method of claim 5 wherein the complementing mismatch repair gene is in PMS2.

9. The method of claim 5 wherein the complementing mismatch repair gene is introduced into the one or more selected cells by cell-cell fusion with a mismatch repair proficient cell.

10. The method of claim 4 wherein the testing comprises analyzing a nucleotide sequence of the gene of interest.

11. The method of claim 4 wherein the testing comprises analyzing mRNA transcribed from the gene of interest.

12. The method of claim 4 wherein the testing comprises analyzing an amino acid encoded by the gene of interest.

13. The method of claim 4 wherein the testing comprises analyzing the phenotype of the cell.

14. The method of claim 1 wherein the testing comprises analyzing a nucleotide sequence of the gene of interest.

15. The method of claim 1 wherein the testing comprises analyzing mRNA transcribed from the gene of interest.

16. The method of claim 1 wherein the testing comprises analyzing an amino acid encoded by the gene of interest.

17. The method of claim 1 wherein the testing comprises analyzing the phenotype of the cell.

* * * * *